(12) United States Patent
Mushahwar et al.

(10) Patent No.: US 8,874,223 B2
(45) Date of Patent: Oct. 28, 2014

(54) MITIGATION OF PRESSURE ULCERS USING ELECTRICAL STIMULATION

(75) Inventors: Vivian K. Mushahwar, Edmonton (CA); Leandro Rafael Solis-Aguilar, Edmonton (CA)

(73) Assignee: Prev Biotech Inc., Edmonton, AB (CA)

( * ) Notice: Subject to any disclaimer, the term of this patent is extended or adjusted under 35 U.S.C. 154(b) by 87 days.

(21) Appl. No.: 13/550,371

(22) Filed: Jul. 16, 2012

(65) Prior Publication Data

US 2012/0316629 A1  Dec. 13, 2012

Related U.S. Application Data

(63) Continuation-in-part of application No. 12/900,164, filed on Oct. 7, 2010, now abandoned, which is a continuation-in-part of application No. 12/362,725, filed on Jan. 30, 2009, now abandoned.

(60) Provisional application No. 61/025,472, filed on Feb. 1, 2008.

(51) Int. Cl.
| | |
|---|---|
| *A61N 1/00* | (2006.01) |
| *A61N 1/04* | (2006.01) |
| *A61N 1/32* | (2006.01) |
| *A61N 1/36* | (2006.01) |

(52) U.S. Cl.
CPC ............... *A61N 1/322* (2013.01); *A61N 1/0452* (2013.01); *A61N 1/36003* (2013.01)
USPC ................................ 607/48; 607/50; 607/116

(58) Field of Classification Search
CPC ..... A61N 1/05; A61N 1/0051; A61N 1/0558; A61N 1/0452; A61N 1/36003
USPC ....................................... 607/115–118, 48, 50
See application file for complete search history.

(56) References Cited

U.S. PATENT DOCUMENTS

| | | | |
|---|---|---|---|
| 4,727,878 | A | 3/1988 | Levine |
| 6,051,017 | A * | 4/2000 | Loeb et al. .................... 607/1 |
| 6,175,764 | B1 | 1/2001 | Loeb et al. |
| 6,393,326 | B1 | 5/2002 | Nachum |
| 6,941,173 | B2 | 9/2005 | Nachum |
| 2003/0050675 | A1 | 3/2003 | Nachum |
| 2003/0093131 | A1 | 5/2003 | Loeb et al. |
| 2004/0267333 | A1 | 12/2004 | Kronberg |
| 2005/0033387 | A1 | 2/2005 | Buchner |
| 2005/0187586 | A1 * | 8/2005 | David et al. .................... 607/9 |
| 2010/0268300 | A1 * | 10/2010 | Ramos Leal et al. ........... 607/50 |
| 2011/0046432 | A1 * | 2/2011 | Simon et al. .................... 600/14 |

* cited by examiner

*Primary Examiner* — Catherine Voorhees
(74) *Attorney, Agent, or Firm* — Marsh Fischmann Breyfogle LLP; Jonathon A. Szumuy

(57) ABSTRACT

A method is provided for treating pressure ulcers by transmitting an electrical stimulus sufficient to effect contraction of a loaded muscle, wherein the method comprises the steps of providing an electrical transmission for effecting contraction of the loaded muscle, transmitting sufficient electrical stimulation to the muscle to contract it for a predetermined short period of time, and ceasing transmission of the stimulus to the muscle for a predetermined longer period of muscle relaxation, whereby the predetermined period of relaxation is sufficient to minimize muscle fatigue and cause sustained reoxygenation.

25 Claims, 22 Drawing Sheets

Simultaneous application

OR

Alternating application

OR

MITIGATION OF PRESSURE ULCERS USING ELECTRICAL STIMULATION

CROSS-REFERENCE TO RELATED APPLICATIONS

This application is a continuation-in-part of U.S. patent application Ser. No. 12/900,164, filed Oct. 7, 2010, now abandoned, which is a continuation-in-part of U.S. patent application Ser. No. 12/362,725, filed Jan. 30, 2009, now abandoned, which claims priority of U.S. Provisional Patent Application No. 61/025,472, filed Feb. 1, 2008, each of which is incorporated herein by reference in its entirety.

FIELD OF THE INVENTION

This invention relates to mitigation of pressure ulcers and, in particular, the prevention of pressure ulcers by means of electrical stimulation.

BACKGROUND

Pressure ulcers (also known as "bed sores" or "pressure sores") are typically associated with individuals having compromised mobility or lack of sensation, such as the infirm, elderly and people suffering from stroke, spinal cord injury, bone and joint disease, vascular pathologies, tumours and diabetes. People in intensive care units, hospital wards, or undergoing long surgical procedures are also at risk of developing pressure ulcers.

A pressure ulcer is a tissue abnormality or lesion resulting from pressure imposed upon soft tissue underlying skin, fat, fascia, muscle, bone, or any combination thereof. Following prolonged periods of loading (e.g., compression and shear), the soft tissue positioned between a bony prominence (e.g. the ischial tuberosities, trochanter, shoulder blades, sacrum) and an external surface (e.g. bed, wheelchair) begins to break down or deform. Soft tissue breakdown results from the occlusion of capillaries and ischemic reduction of blood flow (i.e. a reduction of oxygen, nutrients, and removal of metabolic waste products) to the loaded tissue region.

Ischemia, therefore, has historically been considered a major factor leading to pressure ulcer formation. Paradoxically, the restoration of blood flow, vital to preserving tissue viability, has also been identified to cause extended damage of the tissue. In addition to the injury caused by biochemical changes occurring during tissue ischemia and ensuing reperfusion, high stress levels at the bone-muscle interface and the duration of their application have also been reported to be direct causes of tissue injury. Furthermore, injury to the muscle result in the formation of scar tissue, thus creating more foci for increased stress and leading to injury of adjacent previously healthy tissue. It is the combined effects of these processes that cause the edema, inflammation and necrosis that ultimately leads to the formation of a pressure ulcer.

Pressure ulcers can be initiated at the dermis, usually in the presence of excessive friction and/or compromised dermal integrity, and progress inwardly towards the deeper layers of tissue ("outside-in ulcers"). Alternatively, pressure ulcers can be initiated in the deep tissue, such as at the site of the bone-muscle interface, and evolve outwardly forming a severe pressure ulcer encompassing damage to muscle, fat and skin. Such ulcers, known as "inside-out ulcers", result from muscle breakdown due to prolonged pressure causing sustained and damaging mechanical deformation of muscle and ischemic reduction in blood flow to the tissue.

Muscle is considered to be more susceptible than dermis to tissue degradation from mechanical loading and oxygen deprivation. The National Pressure Ulcer Advisory Panel defines inside-out pressure-related injury to deep tissue under intact skin as "deep tissue injury" (DTI). Unlike outside-in ulcers, non-invasive and clinically viable methods for early detection of DTI currently do not exist, to our knowledge. In present clinical practice, pressure ulcers are normally detected by visual inspection of the skin, which often belies existing extensive damage occurring in deeper tissue. Therefore, DTI can be perilous, as it can develop and evolve undetected by the patient or care giver until a significant destruction of the tissue has already occurred.

Current techniques employed to prevent inside-out and outside-in pressure ulcer formation include frequent repositioning of the patient, and the use of specialized cushions and mattresses that provide some pressure relief of the tissues at risk. However, effective administration of these pressure-relieving techniques is difficult, expensive and often dependent upon patient compliance. Repositioning of patients must achieve prolonged pressure relief to the tissue and must be performed either by hospital staff or by encouraging the patient to perform wheelchair push-ups or side-to-side leans. Specialized mattresses and cushions are heavy, expensive and not widely utilized. Further, these techniques merely provide passive tissue load reduction, thereby failing to actively engage the patient's own muscles.

Electrical stimulation of muscle tissue, commonly referred to as electrical muscle stimulation or "EMS", has been examined as a means for preventing pressure ulcer formation and DTI. For example, EMS treatment has been used with the objectives of:

1. Increasing muscle mass (bulk) in atrophied muscle, thereby improving the cushioning capacity of the muscle, or,
2. Relieving pressure, albeit intermittently, by inducing "lifting" movements of loaded muscles (i.e. inducing changes in seating interface pressure distribution).

EMS to Build Muscle Mass

Having regard to the first technique, EMS may be used as an exercise modality to increase the muscle mass of a particular muscle or muscle group. For example, in order to build mass, EMS may be used to stimulate contraction of a muscle during a "work-out" session (i.e. up to one hour per day), wherein the target muscle is continuously contracted or "activated" for a brief duration (i.e. 5 seconds) and then relaxed or "deactivated" for a brief rest period (i.e. 5 seconds) for the duration of the work-out session. Following daily work-out sessions for prolonged periods (i.e. for up to ~3 months), increases in muscle mass can be achieved. Increases in muscle mass provide greater cushioning capacity of the muscle and passively improve the static distribution of pressure around bony prominences. Patients receiving treatment in this manner have been shown to be capable of withstanding longer durations in a wheelchair than previously possible due to their atrophied muscles.

As with specialized cushions or mattresses, however, one primary disadvantage of this technique is that any benefits gained during EMS treatment of the loaded muscle (e.g., increase in muscle mass) are abolished when the work-out sessions are discontinued. In addition, in order for the treatment to be effective in reducing pressure sores, the target muscle or muscle groups must be capable of generating minimum threshold forces without becoming fatigued during the work-out. When the fatigued muscle can no longer contract, the work-out must be discontinued and the beneficial effects of the treatment are lost.

Pre-conditioning of the muscle prior to treatment has been utilized as a means of increasing fatigue resistance, thereby enabling the muscle to withstand longer bouts of treatment. As with building muscle mass, however, pre-conditioning can be a laborious task necessitating that electrical stimulation be applied to the muscle daily for several months immediately prior to commencing treatment.

There is a need, therefore, for a treatment that provides effective reduction in DTI pressure sores that does not fatigue the muscle.

EMS to Induce Lifting

Having regard to the second technique, EMS may be used to mimic the temporary relief in pressure that is achieved when a patient is repositioned. It is known that EMS applied directly to the loaded muscle may be utilized to change the shape of that muscle (Levine et al., 1990, *Archives of Physical Med & Rehab*, 71:210-215). One main disadvantage of this technique, however, is that individuals who suffer from sustained and appreciable muscle atrophy still require prolonged EMS stimulation or pre-conditioning for lifting treatment of the loaded muscle to be effective.

In an alternative approach, EMS may be applied to the muscles surrounding the loaded muscle. One technique involves applying EMS to the muscles around a patient's hips or knee, such as the quadriceps muscles (Ferguson AC. et al., 1992, *Paraplegia*, 30(7) 474-478), or hamstring muscles (Kaplan HM, et al., 2006, 11th Annual Conference of the International FES Society Proceedings, 112-114), to effect lifting of the (loaded) buttocks from the seating surface. In this approach, however, the patient must be securely stabilized (i.e. restrained) on the seating surface to effectively induce lifting of the target muscle from the seating surface. Further, where EMS is applied to muscles other than those muscles that are directly loaded due to sitting, the patient should be in a seated position and be strapped to the seating surface during treatment. The patient's legs may also be restrained such that when the quadriceps or hamstrings are stimulated to lift the buttocks, lifting movement at the hip is enabled, but movement around the primary joint (i.e. the knee) is prevented. Such restraint of the patient can lead to complications associated with reduced stability of the wheelchair user and/or fracture of weak bones.

There is a need, therefore, for an EMS treatment that does not require pre-conditioning or "lifting" of the loaded muscle.

Despite the foregoing attempts to use unloading or EMS, no single treatment has succeeded in preventing pressure ulcers effectively. The incidence rates of pressure ulcers remain as high as they were nearly half a century ago. Recognizing the absence of a significant reduction in the incidence of pressure ulcers, new preventative interventions are needed, especially for DTI.

SUMMARY OF THE INVENTION

A method is provided for mitigating pressure ulcers in a person by subjecting the person to repeated cycles of electrical stimulation of a loaded muscle, to effect contraction thereof, said stimulation being applied for a short period of time, followed by a cessation of stimulation for a longer period of time, to allow the muscle to relax, wherein the short and longer periods of time are selected to prevent or minimize muscle fatigue.

A "short" period of electrical stimulation time may comprise a duration of time in the order of seconds up to one minute (e.g. 60 seconds or less), and a "longer" period of muscle relaxation may comprise a duration in the order of minutes up to one hour (e.g. 60 minutes or less).

Electrical transmission means may be at least two electrodes positioned on the skin of a person to provide electrical stimulus sufficient to effect contraction of the muscle underlying the skin. Electrical stimulation causes active contraction of the person's own muscle, thereby dynamically deforming and reshaping the muscle to reduce damage caused by mechanical compression of the muscle and restoring blood flow and increasing oxygenation to the loaded tissue.

Reconfiguration of loaded muscle tissue during the short electrically-induced activation period of time temporarily redistributes pressure away from the loaded tissue, thereby mimicking a form of muscle deformation or reshaping that occurs in able-bodied individuals during postural weight shifting or "fidgeting", without lifting the person's body from the seating interface.

Further, reconfiguration of the loaded muscle tissue during the electrically-induced short activation period of time, followed by a predetermined, longer relaxation period of time, restores blood flow and tissue oxygenation to the muscle, thereby reducing damage caused by long periods of ischemia and reperfusion. Sustained restoration of tissue oxygenation (i.e. for an order of minutes in duration) during the predetermined relaxation period of time occurs independently of muscle mass, prevents or reduces muscle fatigue from occurring during treatment, and occurs without the need to precondition the muscle prior to treatment.

By way of example, during the activation period of the electrical stimulation, the stimulation pulses may be applied to a loaded muscle, either continuously (sustained throughout the entire activation period) or discontinuously. The activation period may comprise a predetermined "short" period of time in the order of seconds up to one minute such as, for example, at least 5 seconds and less than 60 seconds, and preferably 10 seconds. The short activation period may be, followed by the cessation of stimulation, causing muscle relaxation, for a longer predetermined relaxation period in the order of minutes up to one hour such as, for example, at least 5 minutes and less than 60 minutes, and preferably 10 minutes. The treatment pattern of intermittent muscle activation followed by muscle relaxation attempts to minimize or prevent muscle fatigue and may be repeated for at least one hour up to 24 hours per day.

The person may be disposed in a variety of positions, such as for example, either a supine or recumbent position during the electrical stimulation treatment. Further, the stimulation may be applied through electrodes implanted near a nerve or muscle.

BRIEF DESCRIPTION OF DRAWINGS

The invention will better be understood when consideration is given to the following detailed description thereof. Such description makes reference to the annexed drawings wherein:

FIG. 6a); (b) quantitative T2* imaging of the gluteus maximus muscles under different conditions (i.e. no weight/unloaded, weight applied/loaded and weight applied+electrical stimulation)

DETAILED DESCRIPTION OF PREFERRED EMBODIMENTS

A method for mitigating or preventing formation of pressure ulcers by transmitting electrical stimuli to a loaded muscle is provided.

Figure 10:
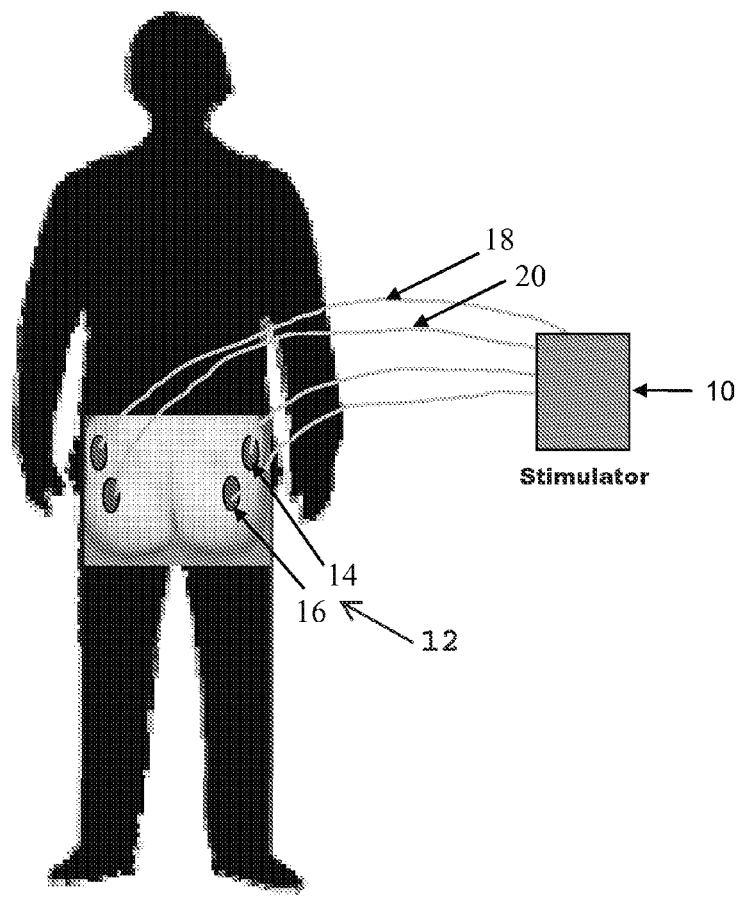
FIG. 10 is a schematic illustration of a system for effecting the mitigation or prevention of formation of pressure ulcers by transmitting an electrical stimulus to the skin of a human patient.

Electrical Transmission Means:

The source of the electrical transmission comprises a stimulator 10, which is electrically coupled to an electrode 12, having an anode 14 and a cathode 16, via electrical leads 18 and 20, respectively (FIG. 10). The stimulator 10 provides an electrical signal, such as, for example, a discrete signal (eg. pulsatile waveform), a continuous signal (eg. sustained sinusoidal waveform, rectangular waveform), or a combination of a discrete signal and a continuous signal. The electrical signal may be transmitted at a characteristic frequency of 20 Hz to 60 Hz, and preferably, the electrical signal is transmitted at a characteristic frequency of 40 Hz. The stimulator 10 may be battery operated.

The electrode 12 is positioned on a person's skin such that the electrical stimulus is transmitted to skin underneath which lies the nerve controlling the contraction of a muscle at risk of developing a pressure ulcer. For instance, the electrode 12 may be positioned on a skin portion proximate to the gluteus maximus muscle of the person, where external forces (such as a seating interface) exert pressure upon the gluteus maximus muscle causing the tissue to be compressed and sheared between the skin portion and a bony prominence.

Figure 9A:
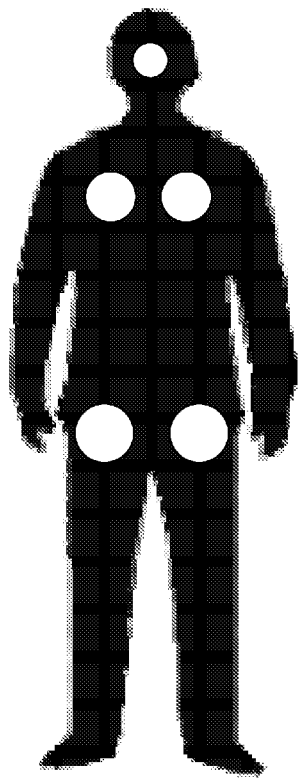
FIG. 9 shows the locations of the electrodes for delivering the intermittent electrical stimulation treatment in a variety of positions in which a patient may be oriented, namely the supine position (9A), the sitting position (9B) and the lateral recumbence position (9C)
Figure 9B:
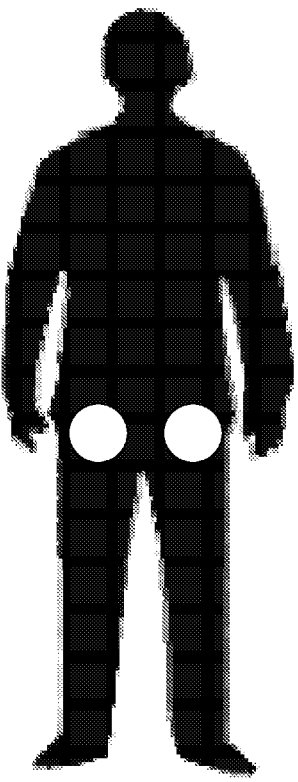
Figure 9C:
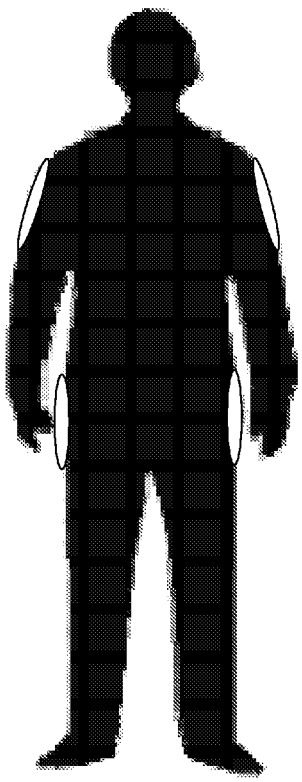

Electrode 12 placement may vary depending upon the position of the person. As shown in FIGS. 9A-9C, where the person is lying in a supine position, the target muscle may be the gluteus muscle, a muscle at least partially surrounding the shoulder blades of the person, or a muscle disposed in proximity to the back of the person's head. Where the person is disposed in a lateral recumbence position, the target muscle may be a muscle of the hip (e.g., gluteus medius and tensor fascia latae muscles) or the side muscles surrounding the shoulder (e.g., deltoid muscle).

Once the electrode 12 is in position, the method comprises transmitting an electrical stimulus to the skin portion of the person. The stimulus should effect contraction of the loaded muscle, wherein the contraction is sufficient to cause the deformation and reshaping of the muscle. The stimulus should cause temporary redistribution of pressure away of the loaded muscle away from bony prominences, thereby temporarily relieving compression and increasing oxygenation of the tissue at risk of developing an ulcer. For example, in one preferred embodiment, the electrical stimulus is sufficient to cause contraction and reshaping of the muscle, but is insufficient to effect lifting of the person (i.e. raising the muscle off the seat of a wheelchair) or movement of the person's limbs (i.e. effecting minimal joint movement).

Movement of the person's limbs may be minimized by transmitting an electrical stimulus that only changes the angle between two bones defining each joint of the person by less than approximately 10 degrees (i.e. upon application of the electrical stimulus, none of the person's joints open or close by more than 10 degrees). In other words, depending upon the position of the person, the electrical stimulus transmitted to the person may cause isometric contraction of the muscle, while causing less than a 10 degree change in the angle of the joint nearest the stimulated muscle.

By way of examples:
where the person is in the sitting position, stimulation of the gluteus maximus would cause isometric contraction of the muscles with less than a 10 degree change in the hip joint angle;
where the person is in the supine position, stimulation of the gluteus maximus would cause an isometric contraction of the muscles with less than 10 degrees change in the hip joint angle and lumbar spine;
where the person is in the supine position, stimulation of trapezius would cause an isomeric contraction of the muscle with less than 10 degrees change in the shoulder joint angle;
where the person is in the supine position, stimulation of the muscles of the back of the head would cause an isometric contraction of the muscles with less than 10 degrees change in the angle of the neck relative to the head;
where the person is in the lateral recumbent position, stimulation of the deltoid would cause an isometric contraction of the muscle with less than 10 degrees change in the shoulder angle;
where the person is in the lateral recumbent position, stimulation of the gluteus medius muscle would cause an isometric contraction of the muscle with less than 10 degrees change in the hip angles;
where the person is in the lateral recumbent position, stimulation of tensor fascia latae would cause an isometric contraction of the muscle with less than 10 degrees change in the hip joint angle or knee angle.

Reducing limb movement allows the person to remain in a supine position or in a recumbence position during treatment, thereby minimizing the need to restrain the person and decreasing the risk of injury or fall.

Electrode burns can be mitigated by measuring the impedance of the electrode-skin interface and by regulating the amount of voltage applied by the stimulator 10 across the interface.

Pattern of Electrical Stimulation:

The stimulator 10 is preferably adapted to transmit an electrical stimulus for short periods of time, in the order of seconds up to a minute (e.g. up to 60 seconds), and repeated every several minutes, for a duration of at least one hour of treatment. Otherwise stated, the person is treated by applying short periods of either continuous or discontinuous stimulation pulses (activation) followed by relatively long periods of relaxation (deactivation), with the objectives of avoiding or minimizing muscle fatigue and enabling reoxygenation of the muscle during the relaxation period. The long periods of relaxation may be in the order of minutes up to one hour (e.g. less than 60 minutes). This cyclic process is repeated over a selected duration, which can be up to 24 hours per day.

Figure 11A:
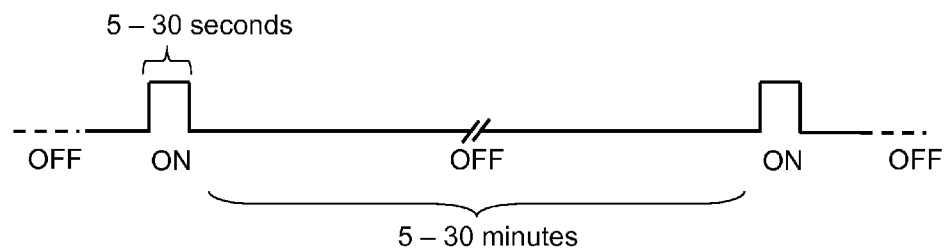
FIGS. 11a, b, c, and d illustrate examples of intermittent electrical stimulation patterns, namely: a basic intermittent electrical stimulation (ON/OFF) pattern (11a); bilateral application of intermittent electrical stimulation pattern (11b), wherein the bilateral application is applied simultaneously to the left and right (top) or applied in an alternating pattern to the left and right (bottom); a variation of intermittent electrical stimulation (ON) pattern (11c, top), wherein the pattern of stimulation during the ON period is sustained or continuous, or wherein the pattern of stimulation during the ON period is discontinuous; and examples of acceptable waveforms of electrical pulses during the ON period (11d).

By way of example, FIG. 11(a) illustrates a basic electrical stimulation pattern, wherein the stimulus may be activated or "ON" for a period of anywhere between 5 to 30 seconds, and then deactivated or "OFF" for a period of anywhere between 5 to 30 minutes. During the ON period, the electrical stimulus, sufficient to effect contraction of the target muscle, activates the target muscle such that it undergoes continuous contraction for the entire ON period (e.g. the entire 5 seconds). Following the ON period, the electrical stimulus is deactivated and the contracted muscle is "relaxed" (i.e. not induced to contract) for the entire OFF period (e.g. the entire 5 minutes). Following the OFF period, the stimulus reactivates the muscle for a second ON period. The second ON period is then followed by a second OFF period, and so on for at least one hour of treatment. This ON/OFF pattern may be repeated for all or substantially all of the treatment period.

In one embodiment of the present method, the ON period will activate the muscle for a duration that is sufficient to effect contraction and to reshape the muscle, while restoring blood flow and increasing oxygenation of the loaded tissue, independent of any changes to muscle mass. For instance, the ON period may have a duration of at least 5 seconds, and preferably a duration of 10 seconds. The stimulation may be applied continuously for the entire ON period, or it may be applied in a "bursting" or discontinuous pattern for the entire ON period. Such brief bouts of stimulation are used to parallel the effects of voluntary or assisted repositioning of the person, and to mimic postural shifting or "fidgeting" observed in able-bodied individuals.

The method will further comprise an OFF period, preferably having a duration of at least 5 minutes, and more preferably 10 minutes in duration. The duration of the OFF period may be any duration of time that provides the target muscle sufficient rest between each ON period of stimulation, thereby reducing muscle fatigue and obviating the need to pre-condition the target muscle prior to treatment. Without sufficient relaxation time during the OFF period, the muscle may become fatigued and require an unacceptable early termination of the treatment.

It is an advantage of the present invention that the muscle being contracted need not be pre-conditioned immediately prior to the treatment. As described above, the purpose of pre-conditioning is to increase muscle mass and muscle endurance (fatigue resistance). Sufficient deactivation (prolonged relaxation) of the muscle during the deactivation period further provides sustained reoxygenation periods following muscle contraction, thereby reducing tissue injury caused by ischemia and/or reperfusion.

Figure 11B:
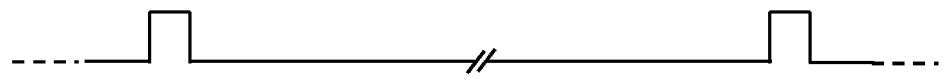
Figure 11B:
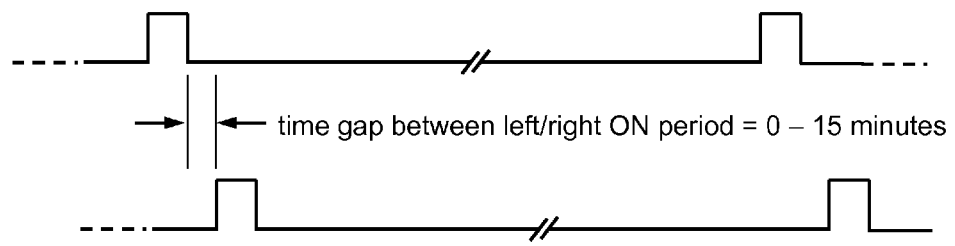

FIG. 11b illustrates an example of intermittent electrical stimulation pattern for bilateral stimulation. Bilateral stimulation refers to the application of the basic ON/OFF intermittent electrical stimulation pattern to muscles on both sides of the body (e.g., left and right gluteus maximus muscles). The ON mode of pattern of stimulation can occur simultaneously to both sides of the body (i.e. the left and right sides are activated at the same time), or stimulation can be staggered (i.e. the right side is activated upon the deactivation of the left side). Where the stimulation is staggered, stimulation of the second side of the body may occur anywhere between immediately up to 15 minutes after the deactivation of the first side of the body.

Figure 11C:
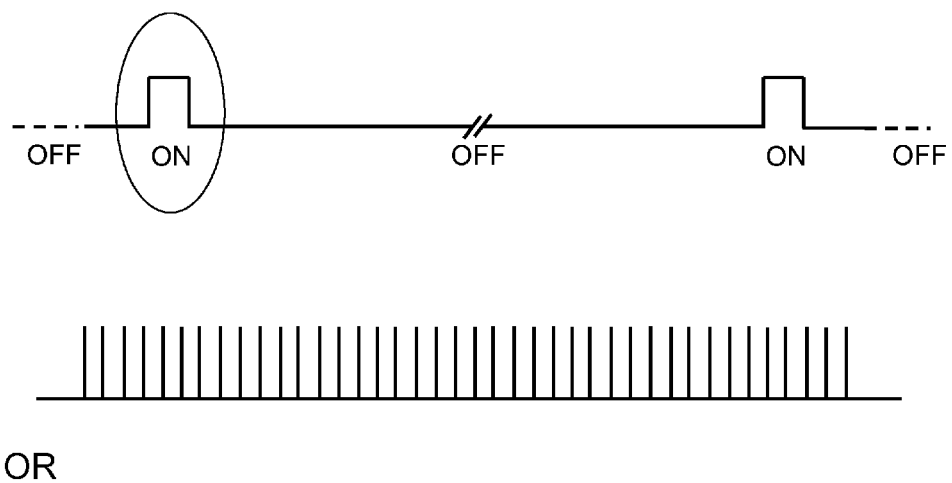
Figure 11D:
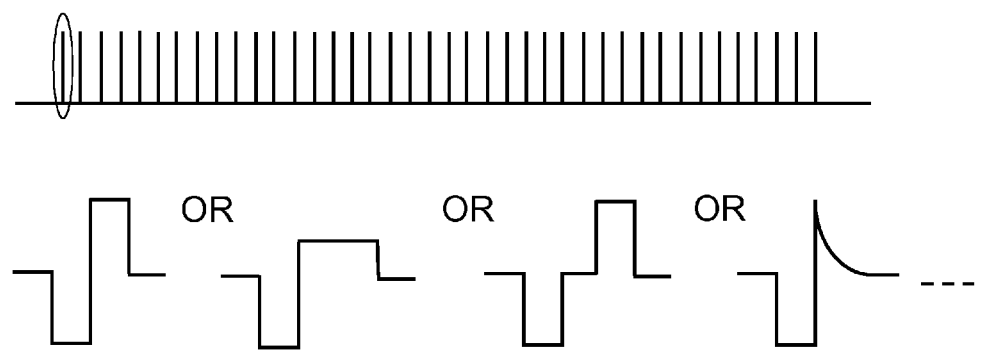

FIG. 11(c) illustrates continuous (or "sustained") and discontinuous applications of the electrical stimulus during the activation "ON" mode of the pattern. FIG. 11(d) illustrates the general waveforms of each stimulus pulse during the ON mode of the pattern.

Unless otherwise indicated, all numbers expressing quantities of ingredients, properties such as distance, operating conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain errors necessarily resulting from the standard deviation found in their respective testing measurements.

Embodiments of the present invention will be described in further detail with reference to the following non-limitative examples.

EXAMPLE NO. 1

Intermittent electrical stimulation may be a useful medical intervention that allows immobilized individuals to remain seated or supine for prolonged periods of time, reducing the frequency of assisted repositioning, and, most importantly, reducing the development of DTI. Experiments have been conducted to investigate the effectiveness of applying intermittent electrical stimulation (IES) to reduce muscle injury due to the presence of persistent external pressure.

Figure 1A:
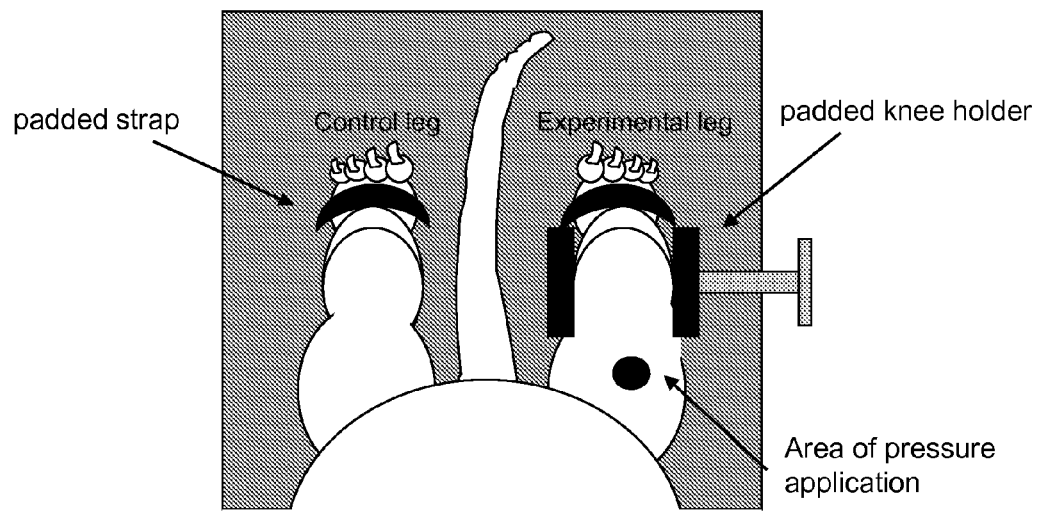
FIG. 1*a* is a top schematic view of the experimental set-up using a rat as the experimental subject, illustrating how constant pressure was applied to the quadriceps muscle of the right hind limb of a rat.

Experiment 1: Effectiveness of IES in the Prevention of DTI in the Rat To investigate the effectiveness of IES in the prevention of DTI, a series of experiments were conducted in four groups of rats:

A Control Group, which received 2 hours of external load applied to the quadriceps muscle of one hind limb, Experimental Group 1, which received the application of pressure and simultaneous application of a 10-s stimulus bout (biphasic, charge-balanced, constant current, 10-40 mA, 250 µs, 50 pulses/s) to the femoral nerve of the experimental leg every 10 minutes throughout the duration of pressure application (see FIG. 1c), Experimental Group 2, which received the same pressure as Group 1 and simultaneous electrical stimulation to the treated leg (10-s bouts) every 5 minutes, and Experimental Group 3, which received the application of IES at 5-minute intervals but without pressure application.

Eighteen adult female, Sprague-Dawley rats were anesthetized with isoflurane (2-3% isoflurane in 500 ml/min oxygen) and a nerve-cuff was implanted around the femoral nerve of each hind limb. Following implantation, each rat was placed on a flat surface with both hind limbs extended and restrained in place with a padded strap positioned around each ankle (see FIG. 1a). The knee and upper calf in the experimental leg were also restrained using a padded clamp to prevent any off-sagittal movement of the leg.

Figure 1B:
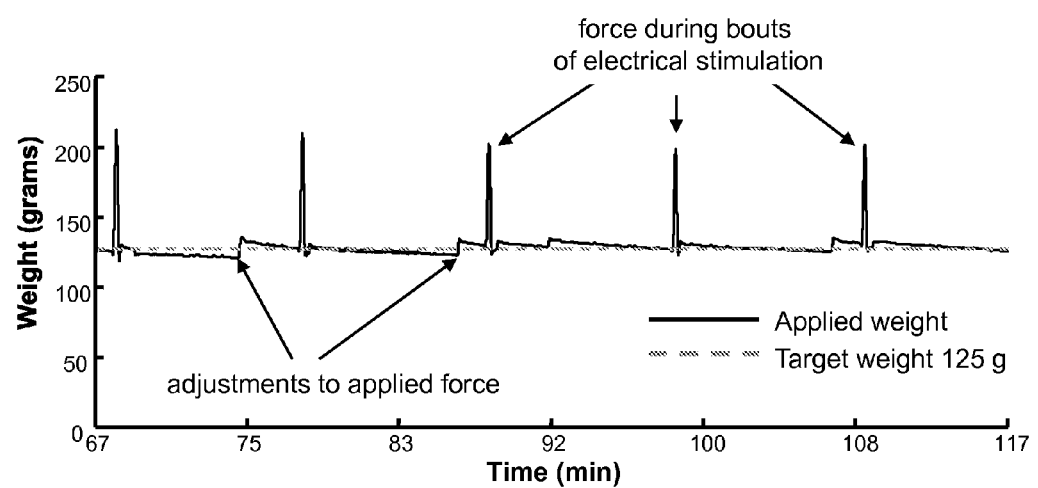
FIG. 1*b* is a graph illustrating a 50-minute record of the force applied to the quadriceps muscle of a rat; the sharp increases in force correspond to the contraction of muscle due to intermittent electrical stimulation (IES)
Figure 1C:
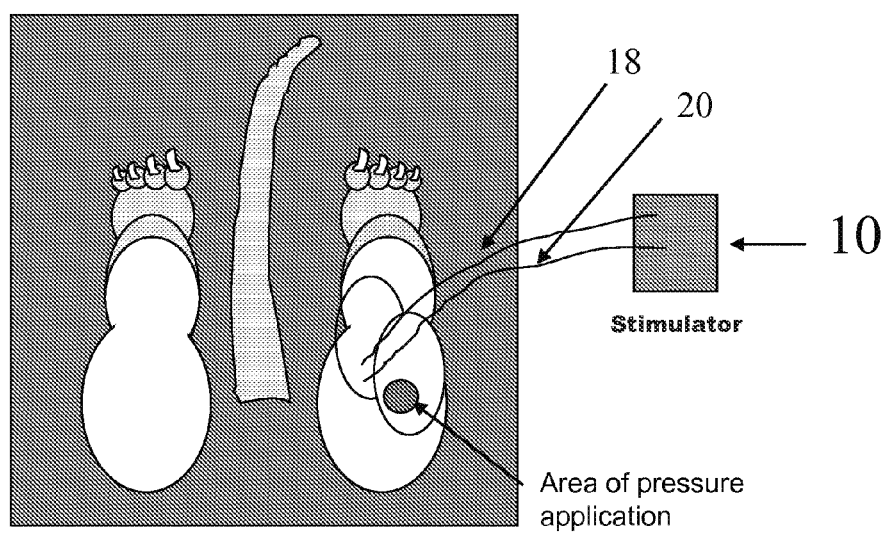
FIGS. 1*c* and 1*d* are top and side views, respectively, of the experimental set up for the rat experiments, illustrating the locations of the electrode and leads for electrical stimulation (input) and the force transducer for measuring the force (output) generated by the contraction of the muscles. Also shown is the indenter that was used to apply external force to the body in order to load the muscle and surrounding tissue to levels that mimic the loading levels experienced by individuals sitting in a wheelchair or lying down in a bed.
Figure 1D:
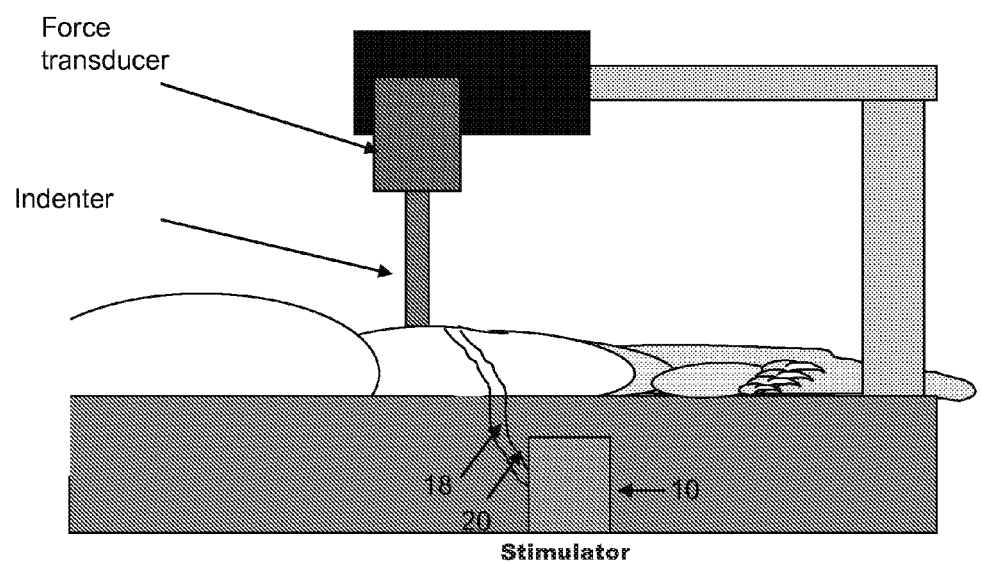

Pressure was applied to the quadriceps muscle of the experimental leg using a 3-mm diameter indenter (see FIG. 1d). Loads were measured with a miniature beam force transducer (Interface, Scottsdale, Ariz., U.S.A.). The force was recorded at a sampling rate of 100 samples/s using a CED Power 1401 A/D board (Cambridge Equipment Design, Cambridge, UK) and SIGNAL 2 software (Cambridge Equipment Design, Cambridge, UK) throughout the duration of the experiment. The indenter was adjusted as required using a micromanipulator (Narishige, Japan) to maintain the desired level of applied force (FIG. 1b). Throughout the experiments, the pressure applied to each group was 164±6.7 kPa for the Control Group, 167±26.6 kPa for Experimental Group 1, and 165.2±25.1 kPa for Experimental Group 2.

In all animals, pressure was applied for a period of 2 hours. Following the period of pressure application, the leg was unloaded, the nerve-cuffs from both limbs were removed and the skin was sutured. Post-operatively, buprenorphine (0.05 mg/kg) was administered subcutaneously, to alleviate any discomfort. The contralateral leg served as an internal control.

Figure 1E:
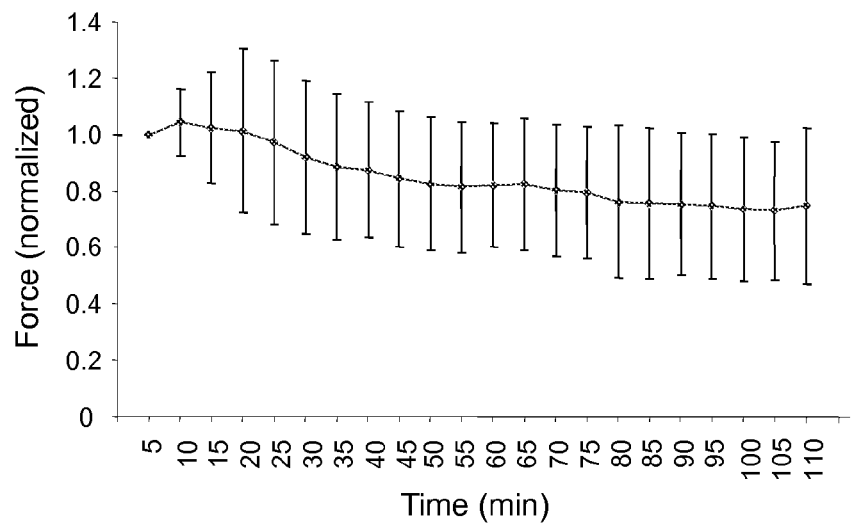
FIGS. 1e and 1f illustrate the force generated by contraction of muscle in response to the intermittent electrical stimulation treatment applied to quadriceps muscles in the rats during two hours of treatment having relaxation periods of: 5 minutes, wherein the force reduced to ~75% of its initial value after 2 hours of application of treatment (FIG. 1e), and 10 minutes, wherein no reduced in the level of force occurred after 2 hours of treatment.
Figure 1F:
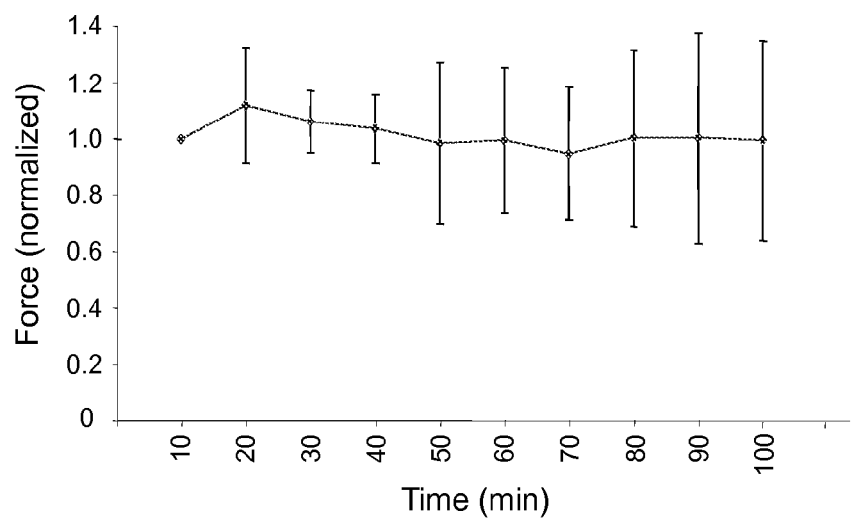

FIG. 1e illustrates the force generated by contraction of muscle in rats in response to IES treatment during 2 hours of treatment. The mean and standard deviation of the force generated by the contraction of the muscle in response to the electrical stimulus during each bout of electrical stimulation over a 2 hour period are shown for 6 rats (top plot) and 5 rats (bottom plot). Bouts of 10 seconds of stimulation (stimulation ON period) delivered every 5 minutes resulted in force reduction of −25% after 2 hours (top plot). This reduction was not significant and did not significantly affect the effectiveness of the treatment. Bouts of 10 seconds of stimulation (stimulation ON period) delivered every 10 minutes resulted in no force reduction after 2 hours (bottom plot).

Deep tissue injury was quantified 24 hours later by in-vivo T2-weighted magnetic resonance imaging (MRI) and post mortem histological assessment of the extracted quadriceps muscles. The untreated contralateral legs of all animals served as healthy controls (Contralateral Control Group).

Assessment of Deep Tissue Health Using MRI

Figure 2:
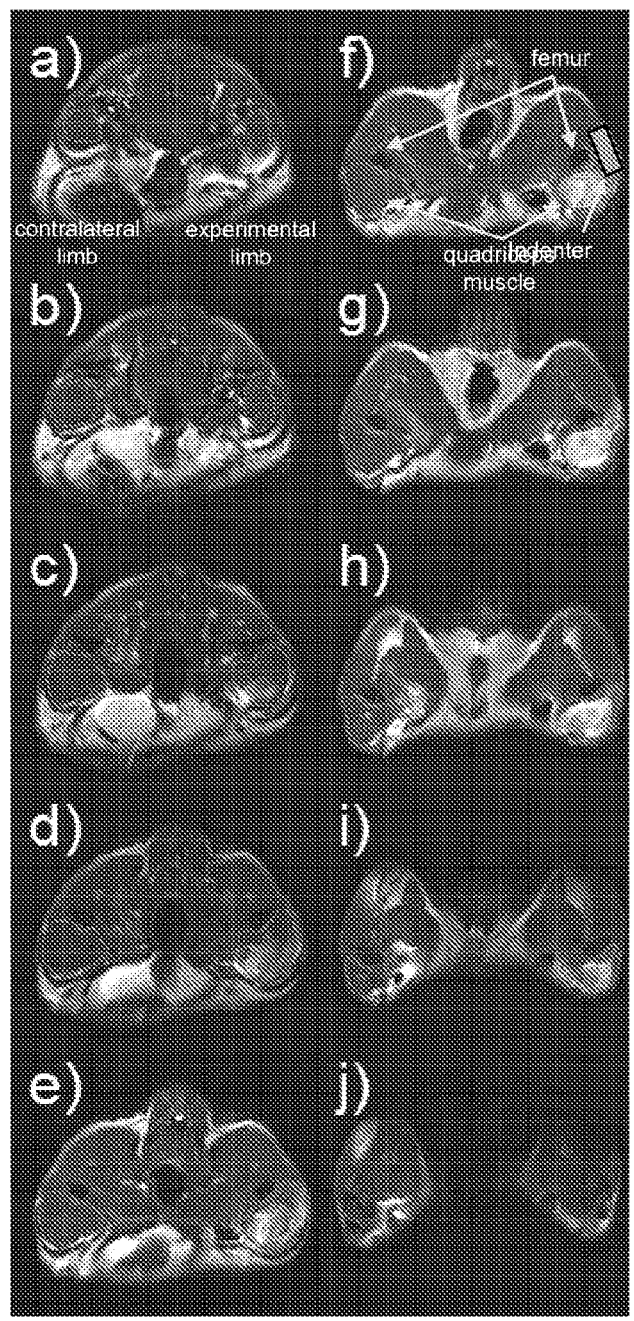
FIG. 2 shows magnetic resonance imaging scans of one animal, illustrating sequential T2-weighted spin echo magnetic resonance images (MRI) of a rat's thigh ranging from the rostral extent of the quadriceps muscle (a) to its caudal end (j), obtained 24 hours after the application of external pressure, with approximate placement of the indenter indicated in slice (f).

Magnetic resonance imaging was used to obtain an in-vivo assessment of deep tissue injury following pressure application, and to quantify the effectiveness of electrical stimulation in preventing such injury in rats. A T2-weighted spin-echo sequence (echo time (TE)=80 ms, relaxation time (TR)=2000 ms) was employed to detect the presence of edema (as indicated by increased water content) within the quadriceps muscles in both hind limbs of each rat. Data were collected during a 30-minute scanning session and twenty MRI slices (images) were acquired from each rat, with slice thickness of 2 mm and slice separation of 1 mm (every other slice shown in FIG. 2). The acquisition matrix size was 256 pixel×256 pixel within a field of view (FOV) of 120 mm×120 mm, resulting in an in-plane resolution of 0.47 mm×0.47 mm. Both hind legs were imaged in the same slice. MRI slices were obtained in the sagittal, coronal and transverse planes in relation to the rat's femur.

Figures 3A, 3B, 3C:
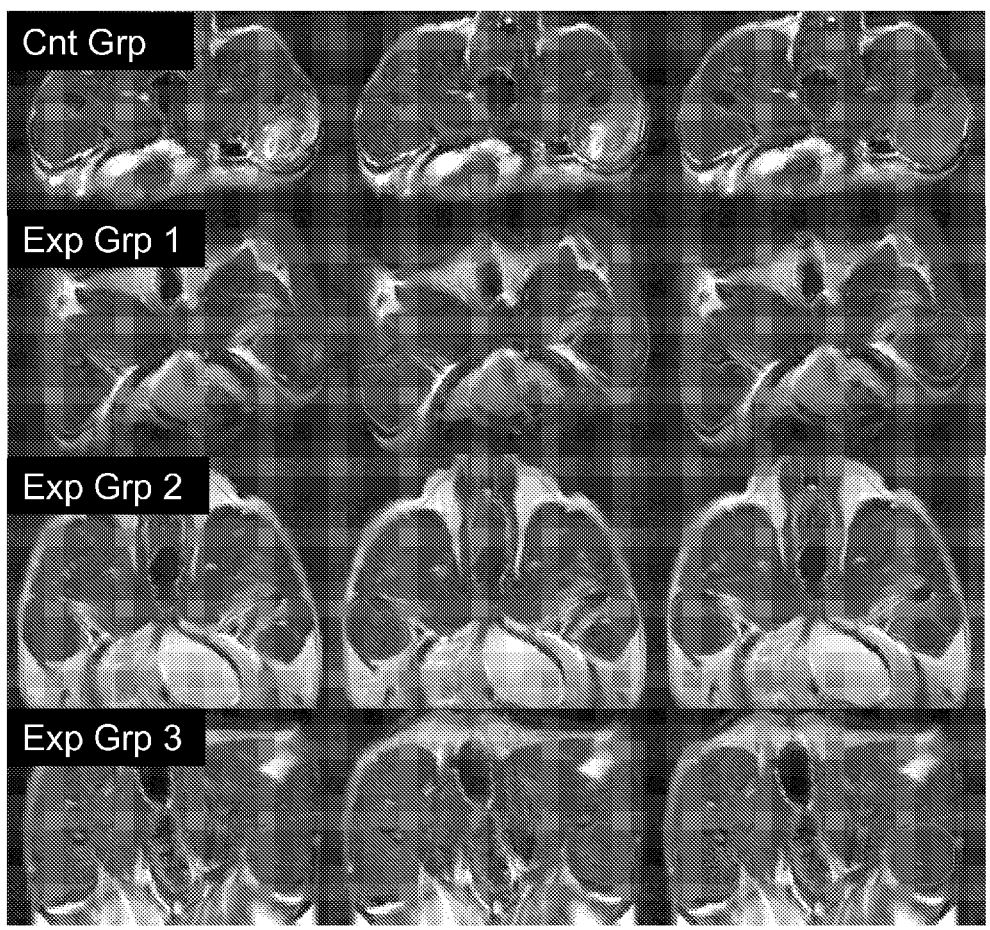
FIG. 3a is a T2-weighted spin-echo magnetic resonance image of rat hind limbs 24 hours after the application of pressure.
FIG. 3b shows magnetic resonance images of the quadriceps muscle.
FIG. 3c shows magnetic resonance images of the quadriceps muscle in both hind limbs, indicating the signal intensity of pixels within the region of the left and right quadriceps muscles; the signal intensity from pixels in the experimental limb was compared to the average±2*standard deviation intensity of those in the contralateral limb, pixels with higher intensity in the experimental limb were marked with red and considered to contain increased water content, pixels with higher intensity than threshold in the contralateral limb were marked with blue as a control; Cnt Grp=control group; Exp Grp 1-3=experimental groups 1-3; Contra Cnt Grp=contralateral control group.

The left and right quadriceps muscles were manually selected from every slice and all analyses were restricted to the pixels inside these two regions (FIG. 3a). To quantify the amount of increased water content present within the experimental leg from each slice, the signal intensity of each pixel in that leg was compared to a threshold intensity level obtained from the contralateral leg (FIG. 3b). The mean±2* standard deviations in the signal intensity from the quadriceps muscle of the contralateral leg was chosen as the threshold intensity level. If the signal intensity of a pixel in the experimental leg was higher than the threshold, the pixel was considered to have increased water content, or edema (FIG. 3c). A percentage of the affected area relative to the total area of the muscle was obtained from each slice and the total affected volume was calculated for each rat by summing the results from all slices. The threshold was also applied to each control (contralateral) limb from each rat to quantify the amount of increased water content that could be attributed to factors other than the application of pressure or IES, such as the electrode cuff implantation or normal variation in the signal intensity. Results from the untreated contralateral limbs of all 24 rats were designated as the Contralateral Control Group.

Histological Assessment

To corroborate the extent of injury in the muscle from the MRI assessment, histological evaluation of the tissue was also performed. Under deep anesthesia (sodium pentobarbital, 40 mg/kg), the animal was transcardially perfused with a formaldehyde (1%)/gluteraldehyde (2.25%) fixative and the quadriceps muscles from both hind limbs were removed. The muscles were photographed, weighed and their volume calculated. The muscle tissue was stored in the same fixative, and subsequently dehydrated through washing in a graded series of ethanol dilutions and embedded in paraffin.

Muscle sections obtained from the region identified by the MR images as containing edema were longitudinally bisected. A 2-3 mm thick longitudinal section was obtained, as well as five 2 3 mm thick transverse sections. A 5 µm slice was obtained from each section and stained with hematoxylin and eosin (H&E).

A veterinary pathologist blinded to the experimental groups performed all histological analyses. A 4.9 mm² area from each slice was assessed to identify muscle fiber necrosis, inflammatory cell infiltration, hemorrhage and tissue mineralization. A necrosis score (0-4) was assigned to each longitudinal slice based on the approximate area exhibiting necrosis out of the slice total area. Subsequently, the transverse slices from each animal were used to confirm the extension of necrosis throughout the muscle. The estimated volume of the muscle affected by necrosis from the histological assessment was compared against the estimated volume of the corresponding muscle affected by edema as calculated from MRI slices.

Results show that edema and tissue injury can develop after a 2-hour application of constant pressure. In all test groups and at the completion of the study, the skin under the pressure indenter did not exhibit any indication of inflammation or injury, underscoring the difficulty of identifying DTI by visual inspection of the skin.

Figure 4:
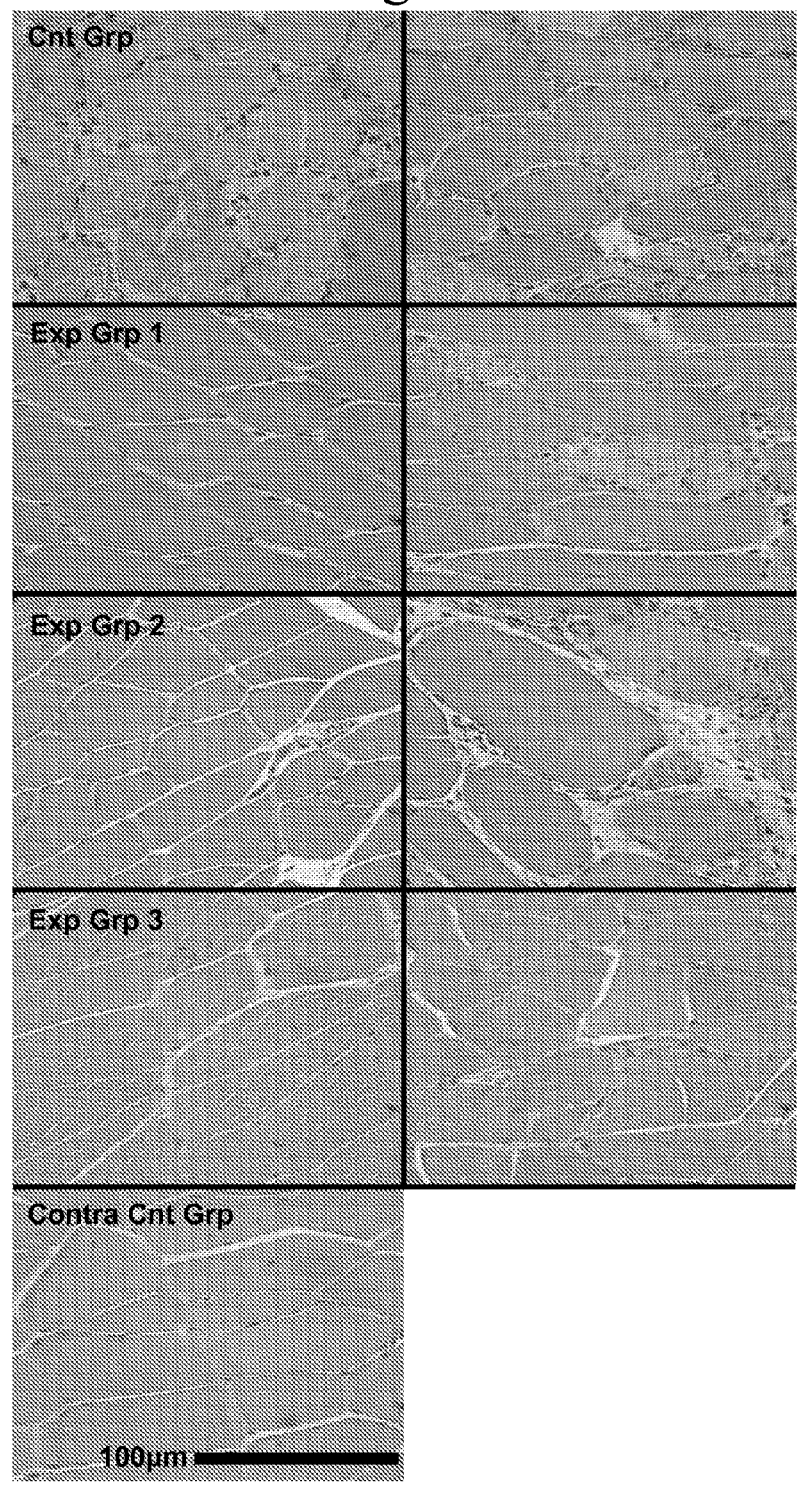
FIG. 4 shows images of sample hematoxylin and eosin-stained cross sections from different animals in each experimental group; Cnt Grp=control group; Exp Grp 1-3=experimental groups 1-3.

As illustrated in FIG. 4, histological assessment of the quadriceps muscle tissue showed that the severity of muscle injury varied between the control and experimental groups. In general, the lesions within the muscle were characterized by swelling, loss of striations, and fragmentation of muscle fibers. The connective tissue surrounding affected muscle fibers was often infiltrated by numerous neutrophils admixed with smaller numbers of macrophages. Hemorrhage into muscle bundles was most apparent in severely affected tissue.

The Control Group had the largest extension of necrotic fibers in the tissue with a score of 3.2±0.8. This score represented a necrotic area occupying 25 to 50% of the area analyzed. The extent of tissue necrosis was significantly larger in the Control Group than that in Experimental Group 1, which had a score of 1.0±0.9 (Kruskal-Wallis non-parametric test, p=0.01), representing a necrotic area of less than 10%. Experimental Group 2 also exhibited a significantly smaller area of muscle necrosis than the Control Group (Kruskal-Wallis non-parametric test, p=0.03), with a score of 1.2±1.5, equivalent to a necrotic area between 10% and 20%. The necrosis score was also significantly smaller in Experimental Group 3 (Kruskal-Wallis non-parametric test, p=0.004), with a score of 0.5±0.6. There was no significant difference between all three experimental groups in the amount of necrosis assessed. The infiltration of neutrophils and macrophages, as well as the presence of red blood cells and mineralization of the tissue, were not significantly different between the control and experimental groups.

Figure 5:
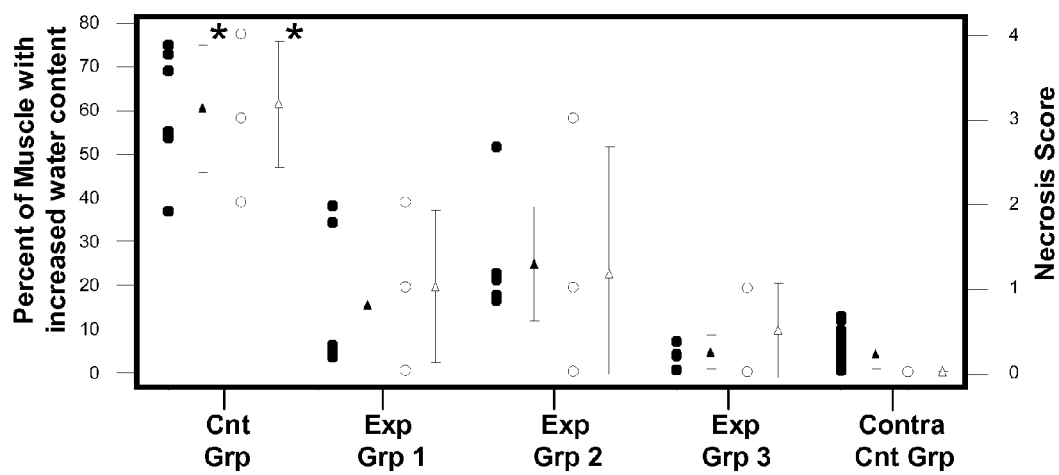
FIG. 5 shows a summary of magnetic resonance imaging and histology results; left axis: individual data points (filled circles) and mean±SD (filled triangles) representing the percent of muscle volume with increased water content (edema) in the quadriceps muscle in all rat groups; right axis: individual data points (empty circles) and mean±SD (empty triangles) representing the necrosis score from the quadriceps muscle in all rat groups; and scoring for quantifying muscle necrosis (per 4.9 $mm^2$ of muscle area) is: 0=no necrosis in region analyzed; 1=0-10% of region analyzed exhibited necrosis; 2=10-25%; 3=25-50%; 4>50% (*represents statistically significant difference, $P<0.05$.

FIG. 5 (right axis, open circles) summarizes the extent of tissue necrosis in the control and experimental groups and illustrates that in the Control Group (pressure, No IES), the application of external pressure for 2 hours generated edema in 60±15% of the muscle. In contrast (FIG. 5, left axis, filled circles), Experimental Groups 1 (pressure+IES every 10 min) and 2 (pressure+IES every 5 min) exhibited a significantly reduced region of edema in the muscle, (16±16% for Experimental Group 1 and 25±13% for Experimental Group 2). Experimental Group 3 (No pressure, IES every 5 min) and Contralateral Control Group (untreated contralateral limbs) exhibited a 5±4% and a 5±4% respectively. The extent of increased water content in all three experimental groups was significantly different from that in the Control Group (one-way ANOVA test, p=0.0001), but was not significantly different from each other (Tukey post-hoc test, Exp 1 vs Exp 2, p=0.59; Exp 1 vs Exp 3, p=0.45; Exp 2 vs Exp 3, p=0.06).

Experiment #2: Mechanisms of Action of IES in the Human

To obtain an insight into the mechanisms of action of IES, the effect of IES on tissue oxygenation was measured in two separate experiments with human volunteers. In the first experiment, tissue oxygenation measurements were obtained from an able-bodied volunteer by means of T2* MRI quantification in muscles in both unloaded and loaded conditions, respectively. In the second, changes in the surface (bed-buttocks interface) pressure profiles generated by the IES-elicited contractions were measured in an able-bodied volunteer.

Tissue Oxygenation in Able-Bodied Human

Figure 7A:
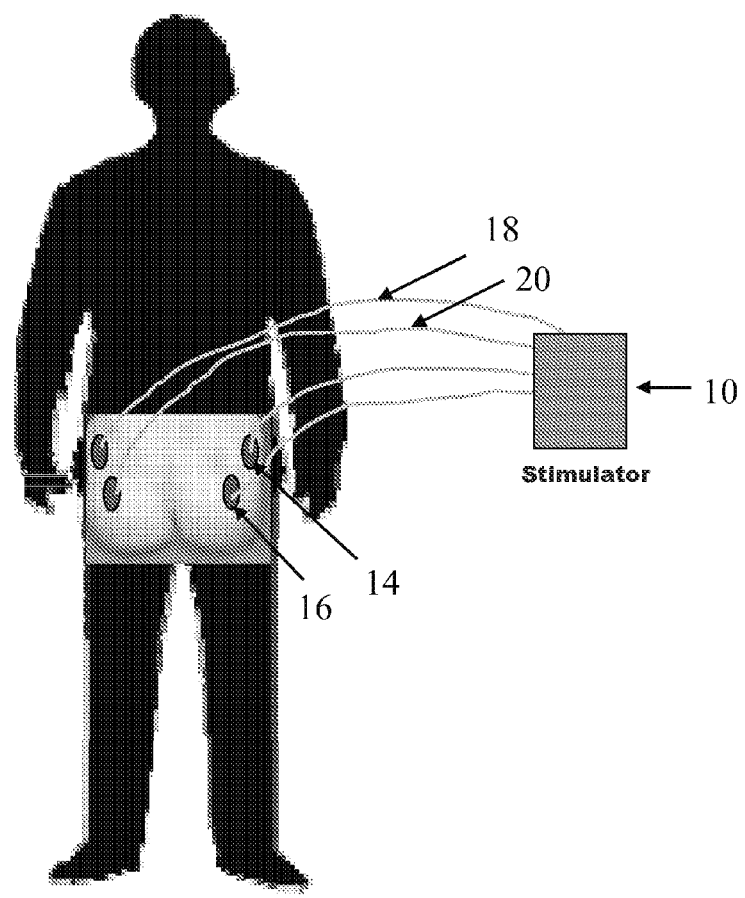
FIG. 7(a) illustrates the experimental set-up for human volunteers.
Figure 7B:
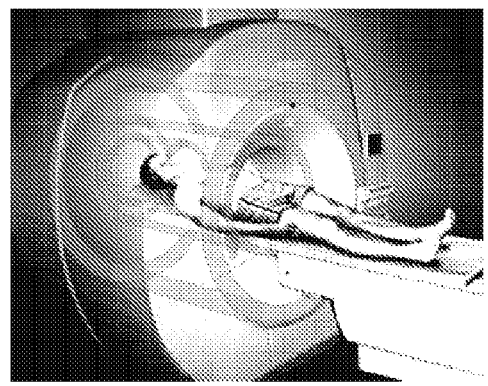
FIG. 7(b) illustrates a human volunteer positioned in the magnetic resonance imaging machine (i.e. 1.5T MRI magnet)
Figure 7C:
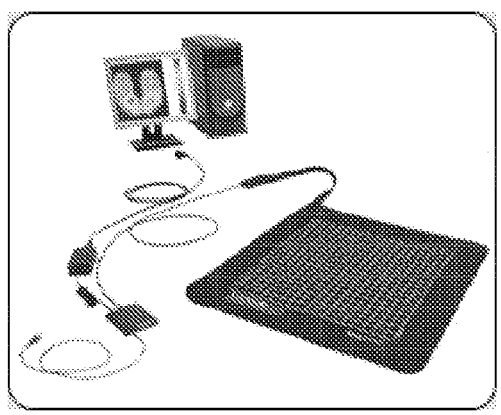
FIG. 7(c) illustrates an example form of superficial pressure measurements (i.e., pressure sensing mat) that may be used to assess outcome of stimulation.

An initial experiment was conducted in an able bodied volunteer (male, 22 yr) to assess changes in tissue oxygenation associated with contractions elicited by IES in an unloaded muscle. The experimental setup is illustrated in FIGS. 7a-7c. Electrodes were placed on the body and electrical stimulation was delivered to induce muscle contractions. The change in the shape of the muscle during contraction, redistribution of surface pressure and changes in tissue oxygenation were measured using magnetic resonance imaging (MRI) techniques and surface pressure mats.

Surface, non-magnetic electrodes were placed over the motor point of the medial gastrocnemius (MG) muscle of one leg. Tissue oxygenation levels were estimated by quantifying changes in the T2* signal in MR scans of the muscle in which an increase in the T2* signal is attributed to an influx of oxygenated hemoglobin to the tissue. MR scans were acquired with a 1.5 Tesla whole body Siemens Sonata scanner (Siemens Medical Solution, Malvern, Pa.) and a 27-cm diameter transmit/receive knee coil circumscribing the lower leg. A custom-prepared multi-gradient-echo sequence (TR=51.8 ms, 8 TEs ranging from 3.6 ms to 47 ms, single slice, 6 mm slice thickness, flip angle=20°, FOV=208 mm×205 mm, readout matrix=160 pixel×158 pixel, in-plane resolution=1.3 mm×1.3 mm) was utilized for all data acquisitions. Baseline levels of oxygenation in MG were obtained as well as simultaneous measurements from the lateral gastrocnemius (LG), medial soleus (MS), and lateral soleus (LS) muscles for comparison. Following the acquisition of baseline scans, successive scans were acquired immediately after 30-s bouts of electrical stimulation delivered through the surface electrodes (biphasic, charge-balanced, constant current, 70 mA, 250 μs, 50 pulses/s).

To mimic a simulated sitting position in which muscles are loaded (e.g., compressed and sheared), albeit around the ischial tuberosities, a second experiment was performed on the gluteus maximus muscles to assess changes in oxygenation levels induced by IES on a loaded muscle. Surface, non-magnetic electrodes were placed over the motor points of the left and right gluteus maximus muscles of an able-bodied volunteer (male, 26 yr). Due to space limitations within the MRI scanner, which prohibits volunteers from sitting upright, muscle compression during sitting was simulated by adding weight over the pelvis of the person lying supine inside a 1.5 Tesla whole-body scanner. Oxygenation measurements were obtained at: 1) rest, 2) with a 20 kg (30% of body weight) load applied over the pelvis, and 3) with a 20 kg load and IES applied simultaneously.

Surface coils placed below the subject and a multi-gradient-echo sequence (TR=90.3 ms, 20 TEs ranging from 3.8 to 89.6 ms, single slice, 8 mm slice thickness, flip angle=30, FOV=223 mm×397 mm, readout matrix=72 pixel×128 pixel, in-plane resolution=3.1 mm×3.1 mm) were utilized for imaging the gluteus in the transverse plane. Three successive 31-s scans were acquired at rest to obtain baseline levels of oxygenation in the left and right gluteus maximus muscles. A 20 kg load was placed over the pelvic region to compress the gluteus muscles and 10 31-s scans were acquired over a 10-minute period of loading. Subsequently, 6 31-s scans were obtained each immediately following a 10-s stimulus bout (biphasic, charge-balanced, constant current, 70 mA, 250 its, 50 pulses/s, 3-s ramp-up, 3-s ramp-down) applied every minute to the gluteus muscles with the load in place. The stimulation parameters utilized did not cause pain or discomfort to the volunteer.

A region of interest (ROI) was selected around each target muscle (MG, LG, SM, and SL, or right gluteus maximus, and left gluteus maximus) in each MR slice, and the T2* levels in each ROI were determined. The T2* values were normalized to their corresponding baseline levels obtained at rest.

Results

Figure 6A:
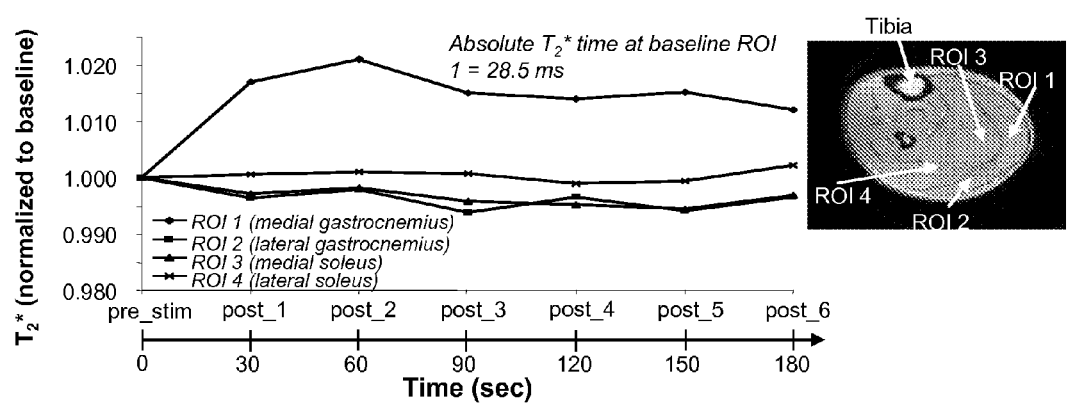
FIGS. 6a, b and c illustrate changes in levels of oxygenation and surface pressure due to loading and electrical stimulation, including: (a) quantitative T2* imaging following six 30-sec bouts of electrical stimulation applied to medial gastrocnemius (persistent regional increases in blood oxygenation were seen with IES)

The effects of IES-elicited contractions on muscle oxygenation were first tested in a condition where the muscle was at rest and unloaded. FIG. 6a summarizes the effect of IES on the level of oxygenation in the muscles of the lower leg. Normalized T2* levels in MG, LG, LS, and MS are shown. Interestingly, IES selectively increased the T2* level of MG, the stimulated muscle. This increase in oxygenation was maintained throughout the experiment. Oxygenation levels in LG, LS, and MS did not show any change when compared to baseline measurements.

Figure 6B:
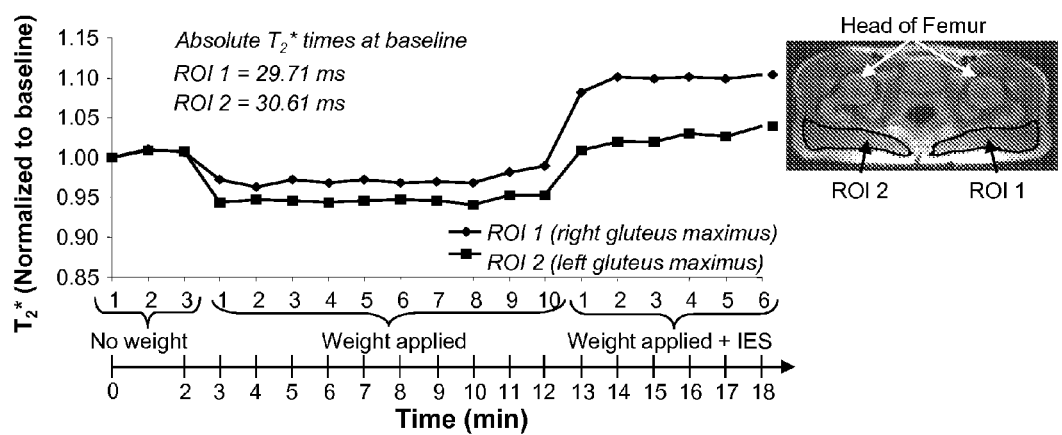
FIG. 6b). A persistent decrease in blood oxygenation was seen when the muscles were loaded, and a persistent increase was obtained with IES; (c) surface-skin interface pressure map of the gluteus muscles under different conditions FIG. 6c). The highest point of pressure with loading was observed around the sacrum (arrows), whereas, with IES, pressure became more evenly distributed, eliminating the previous concentrations of high pressure; ROI 1-4=region of interest 1-4; pre-stim=before electrical stimulation; post 1-6=after 1-6 bouts of electrical stimulation.

The effects of IES-elicited contractions on muscle oxygenation were then examined where the muscles were loaded. These loaded muscles had a corresponding reduction in oxygen supply, a situation that represents the state of tissue around the ischial tuberosities in a seated individual. FIG. 6b summarizes the effect of IES on the level of tissue oxygenation in the gluteus maximus muscles in the presence of an external pressure. Normalized T2* levels in the right and left gluteus maximus muscles are shown for each condition tested (rest, weight, weight+IES). The oxygenation levels in both muscles decreased immediately by −4% after the load application; oxygenation remained at this lower level throughout the 10 minutes in which this condition was maintained. Following IES, the oxygenation levels in the muscles increased above the initial baseline levels by 6%.

Surface Pressure Measurements in Able-Bodied Human

In order to obtain insight into the effects of IES in reshaping the gluteus maximus muscles, and modifying the surface pressure profiles with each contraction, a second experiment was performed. The experiment was conducted in a male able-bodied volunteer, using the same testing conditions as those utilized in the first experiment to assess oxygenation levels in the gluteus maximus muscles: 1) rest, 2) weight, and 3) weight+IES. To elicit contractions in the left and right gluteus maximus muscles, surface electrodes were placed over the motor point of each muscle. The volunteer was placed in a supine position with the buttocks over an X-3 System pressure sensitive mattress (XSensor, Calgary, AB, Canada). Measurements of surface pressure in the sacral region of the buttocks were obtained over a 1-minute period of rest. A 20-kg load, equivalent to 30% of the body weight of the volunteer, was applied over the pelvis to compress the tissue of the buttocks. Surface pressure measurements were acquired for 1 minute under this condition. Electrical stimulation was then applied simultaneously to both gluteus maximus muscles. A series of 3 15-s stimulus bouts (biphasic, charge-balanced, constant current, 70 mA, 250 μs, 50 pulses/s) were applied with the load in place. Changes in surface pressure associated with IES were measured during each bout of stimulation.

Results

In a third experiment (FIG. 6c) surface pressure measurements of the buttocks were obtained under the same three conditions previously tested (rest, weight, weight+IES). The average pressure throughout the buttocks at rest was 10.9 kPa, distributed over a 487 mm2 area. As expected, the region of highest pressure was that surrounding the bony prominence (the sacrum in this case), and exhibited an average pressure of 21.7 kPa.

Following the loading of the pelvis, the average pressure throughout the buttocks increased to 13.9 kPa and was distributed over a 511 mm2 area. The average pressure in the region around the sacrum increased to 25.8 kPa. Simultaneous bilateral application of IES to the loaded (compressed and sheared) gluteus maximus muscles induced contractions which reconfigured the shape of the muscles. The average pressure throughout the buttocks became 14.3 kPa distributed over an area of 424 mm2. However, the average pressure around the sacrum was reduced to 19.5 kPa, a level lower than that seen even during the rest condition.

Figure 8A:
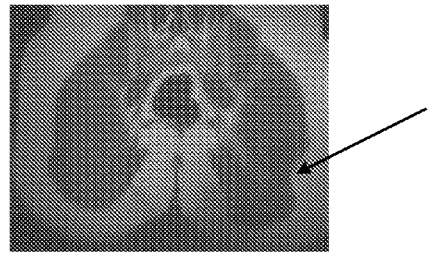
FIGS. 8a, b an c show an MRI of the left and right gluteus muscles of a human demonstrating: the changes in muscle shape during contractions (arrows) induced by electrical stimulation (FIG. 8a); the redistribution of surface pressure (FIG. 8b); and the increase in tissue oxygenation, as estimated from MRI data (FIG. 8c); each during electrical stimulation.
Figure 8B:
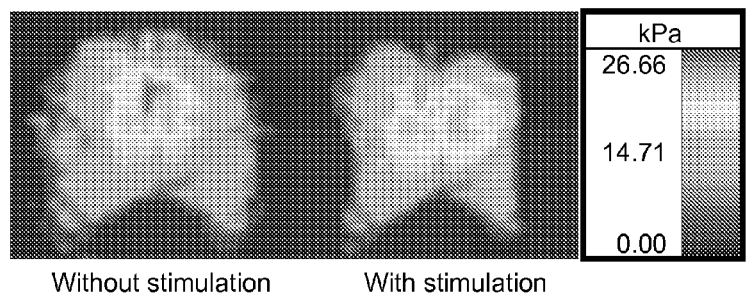
Figure 8C:
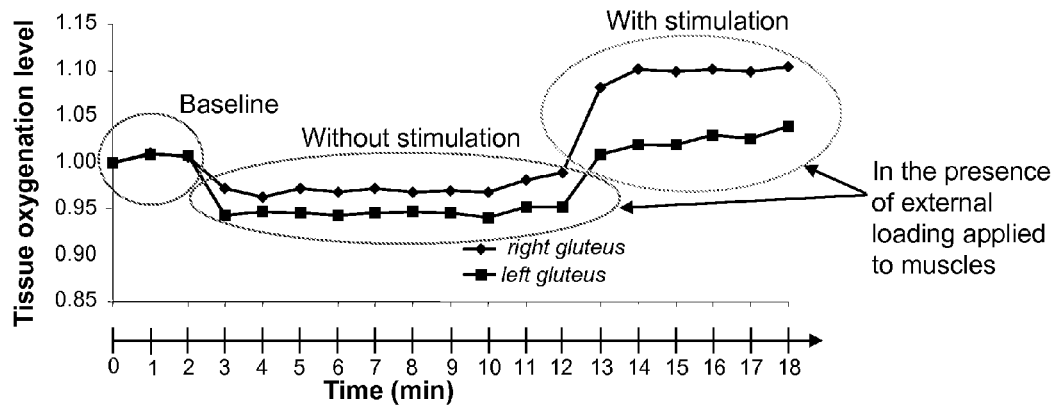

FIGS. 8A-8C illustrate an MRI of the left and right gluteus muscles demonstrating the changes in muscle shape during contractions induced by electrical stimulation (top). They also show the redistribution of surface pressure (middle) and the increase in tissue oxygenation (bottom) during electrical stimulation.

Discussion

The present experiments outline in EXAMPLE NO. 1 examined the efficacy of IES in preventing DTI in a rat model and its mechanism of action in human volunteers. Our results show, that within defined parameters of electrical stimulation, a considerable reduction in DTI was observed. Traditionally, tissue injury generated by ischemia following long periods of tissue compression, has been considered the principal etiological factor behind pressure ulcers. Within this precept, more frequent stimulation should restore tissue oxygenation in the tissue to normal or near-normal levels, potentially eliminating tissue injury caused by ischemia. The finding that there was no significant difference between our experimental groups (IES every 10 minutes vs. 5 minutes) could indicate that the beneficial effects of an increase in oxygenation to the tissue may have reached their threshold when stimulation occurred every 10 minutes. It is possible that the amount of damage observed in both experimental groups could be attributed to damage generated directly by the high stress levels at the bone-muscle interface and excessive cell deformation, a factor that was further exaggerated in our experimental set up due to the fixation of the hind limb which led to an increase, rather than a decrease, in focal pressure during the IES-induced contractions (evident in the increases in recorded force in FIG. 1b). Although the application of pressure to the rats' limbs was done outside the MRI scanner, utmost care was taken in the placement of the indenter, such that it was as centered as possible over the QM and the femur.

Comparison of Experimental Group 3 and the Contralateral Control Group demonstrated that the use of IES as frequently as every 5 minutes does not cause an increase in the water content of the muscle. The minimal amount of water content identified in the Contralateral Control Group, as calculated in this study, indicates that 5% of the tissue water content quantified in the Control Group and Experimental Groups 1 and 2 was not caused by the load application.

It has been suggested that high stress levels at the bone-muscle interface is a primary factor in the development of pressure ulcers, but the extent of tissue injury that is associated with these mechanical forces (shear and stress) has yet to be determined. Although complete elimination of DTI has not been achieved, our results suggest that IES delivered every 10 minutes is sufficient to reduce greatly the extent of damage in deep tissue exposed to constant external pressure.

None of the rats in this study showing indications of DTI displayed injury to the overlying skin. This emphasizes that skin appearance is a poor indicator of deep tissue health, and supports the need for other alternative methods to detect DTI. The results of this study show that MRI is an effective tool for the detection of muscle edema associated with the presence of DTI, even when injury occurs in muscles as small as those in the rat hind limbs (FIG. 3a). Although MRI currently may not be ideal for screening patients with DTI due to cost and availability, in situations where an individual is considered to be at high risk of developing an ulcer or has a long history of ulcer development, it might be necessary to perform periodic screenings. Identifying DTI before it fully evolves into a pressure ulcer would not only have a significant beneficial impact on the health and quality of life of the individual, but could greatly reduce costs associated with further medical and surgical treatments.

Mechanisms of Action of IES

Figure 6C:
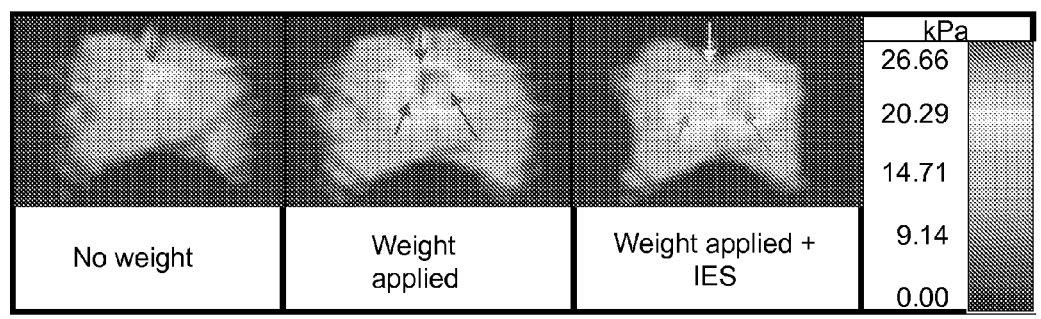

Our results demonstrated that the levels of available oxygen in the tissue of gluteus maximus were reduced immediately after compressing the muscles (FIGS. 6a-6c). However, instantly following the first IES induced contraction of the muscles, the levels of tissue oxygen increased. This increase was greater than baseline levels, and was most likely caused by reactive hyperemia, a process in which there is an increase in blood flow into the capillaries after brief periods of occlusion. This increase in oxygenation was maintained after each of the 6 IES induced contractions. While oxygenation levels in the unloaded medial gastrocnemius muscle also increased with IES, the increase was less than that in the gluteal measurements. This may be due to the fact that blood flow to the medial gastrocnemius muscle was not altered, and consequently oxygenation levels were already at normal levels.

While periodical increases in tissue oxygenation should have the beneficial effect of negating tissue injury associated with ischemia-reperfusion, pressure relief is still needed to prevent further damage from persistent high stress levels of muscle cells. Our results demonstrated that IES of the loaded gluteus muscles reconfigured the shape of the muscles and distributed the pressure laterally in the buttocks. The net result was a periodical relief of the superficial pressure around the bony prominence and reduction in the overall pressure throughout the buttocks. The use of superficial pressure measurements combined with recently developed finite element models of the gluteal muscles which can estimate the stress levels at the bone-muscle interface, could provide a more accurate tool for predicting the risk of developing DTI.

EXAMPLE NO. 2

Experiments were conducted in seated volunteers to evaluate the effect of various parameters of IES on: 1) the redistribution of surface pressure during contraction, 2) changes in the shape of the gluteus maximums muscles around the ischial tuberosities, and 3) changes in tissue oxygenation. Surface pressure mats and magnetic resonance imaging (MRI) techniques were used for the measurements.

Five able-bodied volunteers with intact spinal cord and four volunteers with spinal cord injury (SCI) participated in the study. Four IES patterns were tested between the two groups of volunteers as described in Table 1 below. Electrical stimulation was provided through surface electrodes placed on the motor points of the gluteus maximus muscles of both legs in all volunteers.

TABLE 1

IES parameters tested in volunteers with intact and SCI study participants

| Volunteer | IES ON:OFF periods | Stimulation characteristics during ON period | Stimulation parameters |
| --- | --- | --- | --- |
| Intact | 10 (sec):7 (min) | continuous | 200 µs pulses, 20-120 mA, 40-50 pulses/s |
| | 10 (sec):7 (min) | discontinuous (3 sec on:2 sec off:3 | 200 µs pulses, 20-120 mA, 40-50 pulses/s |
| SCI | 7 (sec):10 (min) | continuous | 200 µs pulses, 20-120 mA, 40-50 pulses/s |

TABLE 1-continued

IES parameters tested in volunteers with intact and SCI study participants

| Volunteer | IES ON:OFF periods | Stimulation characteristics during ON period | Stimulation parameters |
|---|---|---|---|
| | 13 (sec):10 (min) | continuous | 200 µs pulses, 20-120 mA, 40-50 pulses/s |

Redistributions in surface pressure with IES were assessed with the volunteers seated in a regular office chair (intact) or a wheelchair containing a standard pressure relief cushion (SCI). A pressure mat containing a 36×36 array of sensors was placed between the volunteers and the sitting surface. A map of the surface pressure was obtained during the OFF period of IES and compared to that obtained during the ON period.

Surface pressure was highest around the ischial tuberosities in both intact and SCI individuals during the OFF period of IES. During the ON period, contractions of the gluteus maximus muscles generated a redistribution in surface pressure in both intact and SCI volunteers. There were decreases in surface pressure around the high-risk ischial tuberosity regions that are most susceptible to the formation of pressure ulcers. Concomitant increases in pressure in the surrounding areas, low-risk regions, were seen.

Figure 12:
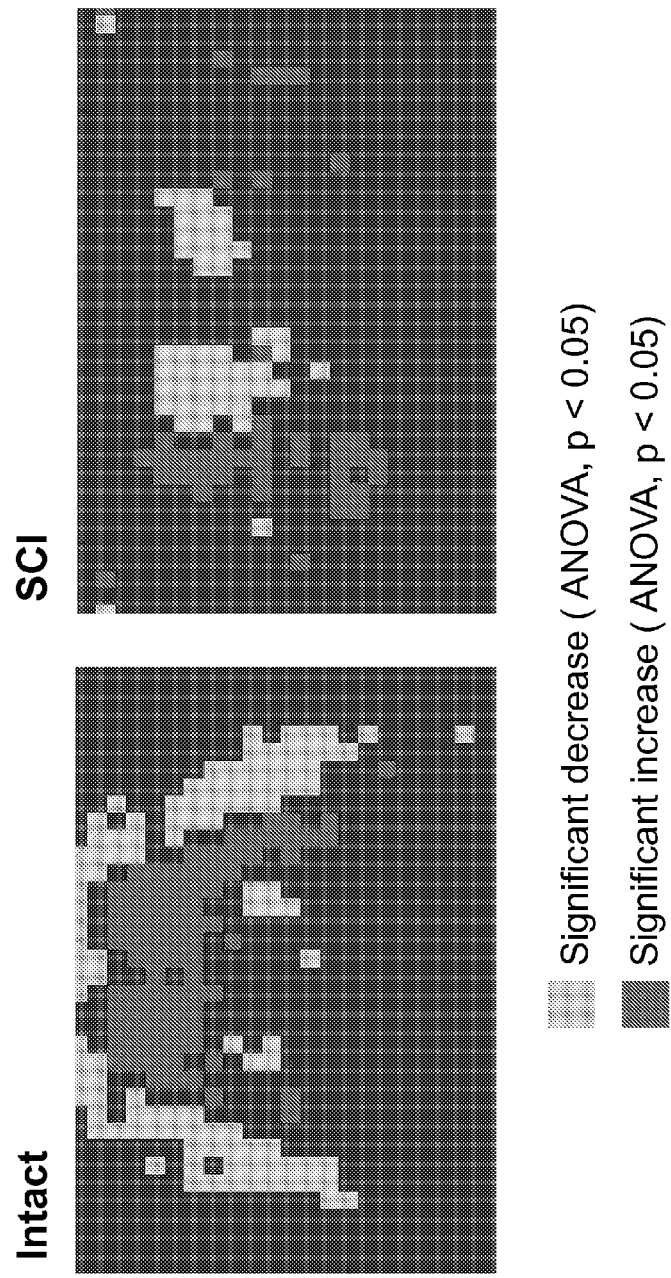
FIG. 12 illustrates quantified pressure mat sensor readings showing reductions in surface pressure around the ischial tuberosities induced by electrical stimulation.

The redistribution in surface pressure produced by IES was quantified by comparing the changes in readings of each of the sensors embedded within the pressure mat during the stimulation ON and OFF periods. FIG. 12 shows a typical example of the distribution of sensors showing statistically significant changes in pressure readings between the ON and OFF periods of IES. Sensors with a significant reduction in pressure readings during the ON period of IES relative to the OFF period are shown in white, those with a significant increase are shown in grey, and those with no significant change are shown in black. During the ON period of IES, significant reductions in pressure were obtained around the ischial tuberosities in both able-bodied and SCI volunteers, regardless of the sitting surface (regular chair vs. wheelchair with pressure relief cushion).

During these experiments, able-bodied volunteers as well as those with SCI who had some preserved sensation around the gluteal region (n=2) reported that IES relieved their discomfort due to long durations of sitting. Furthermore, the relief was sustained for several minutes after the ON period of IES. In comparison to standard clinical practices such as wheelchair push-ups, the volunteers reported that IES provided more relief of discomfort due to sitting and for longer durations. Able-bodied volunteers preferred the continuous mode of stimulation during the ON period of IES over the discontinuous patterns, even though they reported that both patterns produced a similar level of relief of discomfort due to sitting. Because of their altered sensation, the SCI volunteers could not subjectively compare the level of relief produced by the two durations of the continuous mode of stimulation during the ON period of IES (7 vs. 13 seconds).

To investigate the changes in the shape of the muscle produced by IES as well as changes in oxygenation levels of deep tissue, the volunteers were transferred to a custom built MRI-compatible apparatus. This apparatus positioned the volunteers in a manner that mimicked a sitting posture and produced similar surface pressure profiles to those obtained while sitting in a chair/wheelchair.

Figure 13:
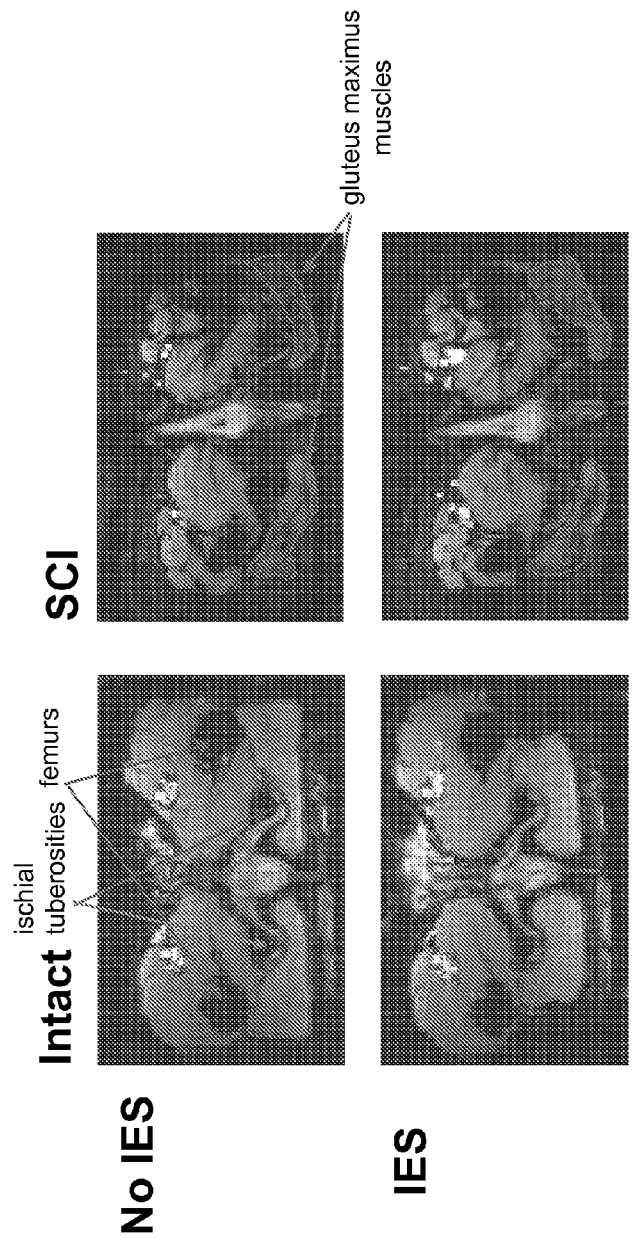
FIG. 13 illustrates magnetic resonance images showing changes in muscle shape during IES.

FIG. 13 provides $T_2$-weighted MRI scans which show the shape of the gluteus maximus muscles at rest (OFF period of IES) and during contraction (ON period of IES) for able-bodied (intact, left) and injured (SCI, right) volunteers. Substantial changes in muscle shape were seen in the intact volunteers (FIG. 13, left). Changes in muscle shape were also seen even in the much atrophied muscles of SCI volunteers (FIG. 13, right). These changes explain the redistributions in surface pressure seen in FIG. 12, and demonstrate that redistributions in internal pressure are also obtained by IES.

Figure 14:
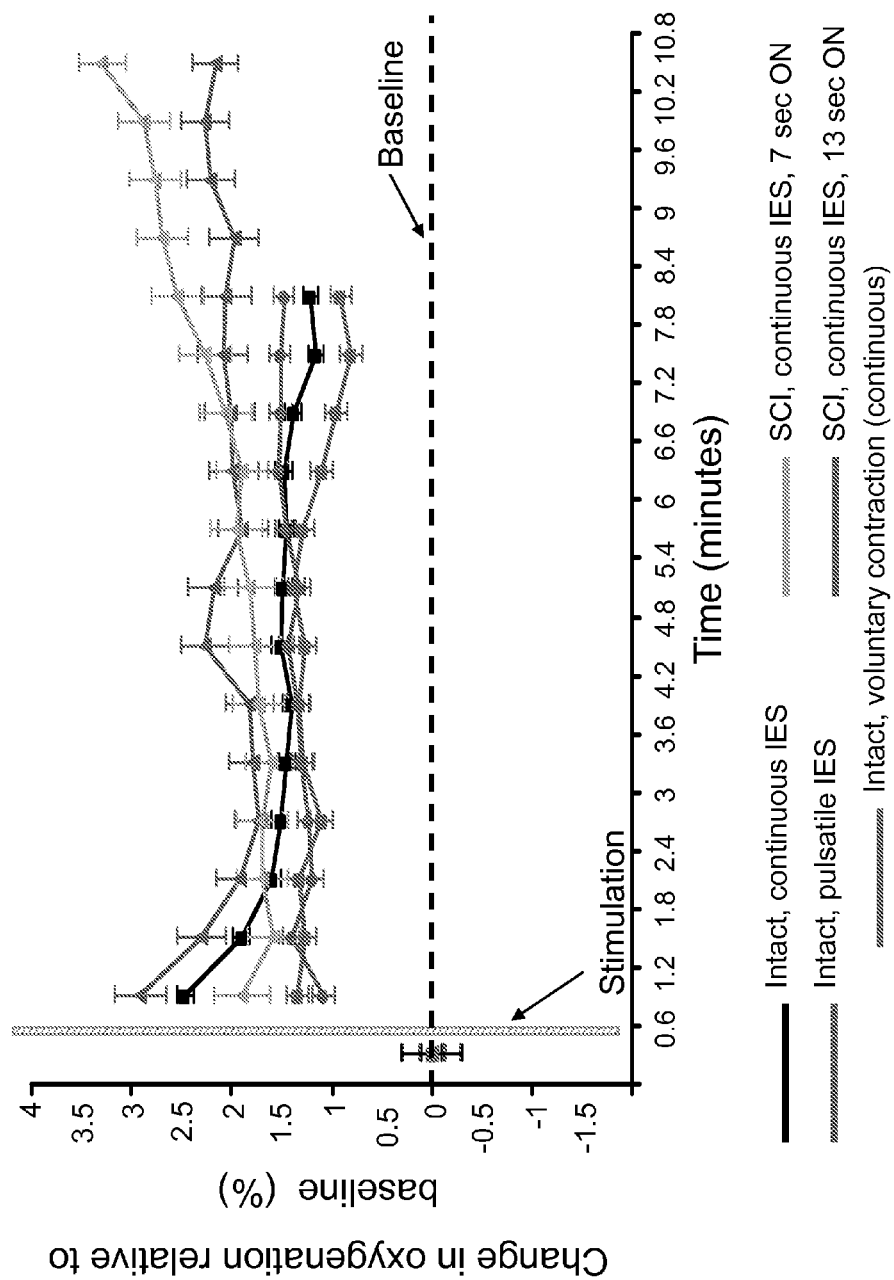
FIG. 14 illustrates sustained increases in tissue oxygenation produced by contractions generated during the ON period of IES.

To assess the changes in tissue oxygenation, T2* MRI images were obtained and alterations in the signal intensity in the gluteus maximus muscles due to IES were quantified as previously described (pages 31-32, FIG. 6a, b). FIG. 14 summarizes the changes in tissue oxygenation (mean±standard deviation) seen in intact and SCI volunteers, and in response to the four (4) patterns of IES tested (Table 1). To compare the changes in oxygenation in response to contractions produced by IES and voluntary activation, the able-bodied volunteers were also asked to contract their gluteus maximus muscles voluntarily and to hold the contraction for 10 seconds (mimicking the 10 sec ON, continuous, IES pattern).

In all cases, significant increases (ANOVA, $p<0.05$) in tissue oxygenation were seen following the ON period of IES. These increases were at times more prominent than those produced by voluntary contraction. Furthermore, the increases in oxygenation were sustained for up to 10 minutes (longest IES OFF period tested to date), which explains the sustained relief from discomfort reported by the volunteers during the surface pressure measurements described above. Very importantly, the pattern of tissue oxygenation observed in volunteers with SCI was similar to that seen in intact volunteers, despite their substantially atrophied muscles. While direct measurements of blood flow or oxygen were not obtained, the increases in oxygenation (1-3% increase in T2* signal intensity) are estimated to reflect a 15-45% increase in blood flow in the gluteus maximus muscles.

Some differences were observed in the level of tissue oxygenation produced by the various patterns of IES. First, the continuous pattern of stimulation during the ON period of IES produced larger increases in oxygenation immediately following the cessation of stimulation compared to the discontinuous pattern. However, by 3 minutes within the OFF period of IES, the oxygenation levels were similar for both the continuous and discontinuous stimulation patterns. Second, longer stimulation durations during the ON period of IES produce larger increases in oxygenation immediately following the cessation of stimulation. However, by 2 minutes within the OFF period of IES, the oxygenation levels were similar for all durations of the ON period of IES tested (i.e., 7, 10 and 13 seconds). Third, the changes in tissue oxygenation produced by the discontinuous pattern of stimulation during the ON period of IES were similar in profile to those produced by voluntary contraction.

In conclusion, the experiments in the seated individuals (intact and SCI) demonstrated that IES is an effective means for redistributing surface pressure, changing muscle shape, and producing sustained increases in deep tissue oxygenation. All tested patterns of IES were effective in achieving these outcomes. Therefore, IES may provide a powerful means for prophylactically preventing the formation of pressure ulcers originating at deep bone-muscle interfaces.

Although the disclosure describes and illustrates various embodiments of the invention, it is to be understood that the invention is not limited to these particular embodiments. Many variations and modifications will now occur to those skilled in the art of hardware. For full definition of the scope of the invention, reference is to be made to the appended claims.

What is claimed is:

1. A method of intermittent electrical stimulation to mitigate pressure ulcers in a person suffering from compromised mobility, altered sensation, or both, causing mechanical deformation of loaded muscles, the method comprising repeating cycles of:
    electrically stimulating the loaded muscle, for a predetermined period of stimulation, to effect contraction sufficient to reshape the muscle, reduce stress levels and restore oxygenation to the muscle, and
    ceasing electrical stimulation of the muscle, for a predetermined period of relaxation longer than the predetermined period of stimulation, allowing the muscle to relax and minimizing fatigue thereof.

2. The method as defined in claim 1, wherein the predetermined periods of stimulation and relaxation are selected to mimic postural fidgeting in able-bodied individuals.

3. The method as defined in claim 1, wherein the predetermined period of stimulation comprises a brief bout of stimulation in the range of seconds and is repeated every several minutes.

4. The method as defined in claim 1, wherein the predetermined period of stimulation is a short period of time in the range of seconds and is repeated every several minutes.

5. The method as defined claim 1, wherein the predetermined period of stimulation is in the range of 5 to 30 seconds.

6. The method as defined in claim 1, wherein the electrical stimulation is pulsed.

7. The method as defined in claim 6, wherein the pulses are transmitted continuously during the predetermined period of stimulation.

8. The method as defined in claim 6, wherein the pulses are transmitted discontinuously during the predetermined period of stimulation.

9. The method as defined in claim 1, wherein the predetermined period of relaxation is in the range of minutes up to one hour.

10. The method as defined in claim 1, wherein the predetermined period of relaxation is at least 5 minutes.

11. The method as defined in claim 1, wherein the predetermined period of relaxation is in the range of 5 to 30 minutes.

12. The method as defined in claim 1, wherein the repeated cycles are continued for at least one hour.

13. The method as defined in claim 1, wherein the electrical stimulation is applied at the person's skin.

14. The method as defined in claim 1, wherein the electrical stimulation is applied through implanted electrodes near a nerve or muscle.

15. The method as defined in claim 1, wherein the predetermined periods of stimulation and relaxation are selected to provide periodically-induced contractions of the muscle paralleling involuntary or assisted repositioning.

16. The method as defined in claim 1, wherein the predetermined period of stimulation is at least 5 seconds.

17. The method as defined in claim 1, wherein the predetermined period of stimulation is in the range of seconds and up to one minute.

18. The method as defined in claim 1, wherein the loaded muscle is not preconditioned.

19. The method as defined in claim 1, wherein the method is for preventing the formation of a pressure ulcer.

20. The method as defined in claim 1, wherein the predetermined period of stimulation is at least 5 seconds and less than 60 seconds, and the predetermined period of relaxation is at least 5 minutes and less than 60 minutes so as to mimic postural fidgeting in able-bodied individuals.

21. The method as defined in claim 20, wherein the cycles are repeated for up to twenty four hours.

22. A method of mitigating pressure ulcers in a person suffering from compromised mobility, altered sensation, or both, causing mechanical deformation of loaded muscles, the method comprising repeating cycles of:
    electrically stimulating the loaded muscle, for a predetermined period of stimulation, to effect contraction sufficient to reshape the muscle, reduce mechanical deformation and stress levels and restore oxygenation to the muscle, and
    ceasing electrical stimulation of the muscle, for a predetermined period of relaxation longer than the predetermined period of stimulation and at least 5 minutes, allowing the muscle to relax and minimizing fatigue thereof.

23. The method as defined in claim 22, wherein the predetermined periods of stimulation and relaxation are selected to provide periodically-induced contractions of the muscle paralleling voluntary or assisted repositioning.

24. The method as defined in claim 22, wherein the predetermined periods of stimulation and relaxation are selected to mimic postural fidgeting in able-bodied individuals.

25. The method as defined in claim 22, wherein the predetermined period of stimulation is at least 5 seconds and less than 60 seconds, and the predetermined period of relaxation is at least 5 minutes and less than 60 minutes.

* * * * *